(12) United States Patent
Kishimoto et al.

(10) Patent No.: US 7,775,984 B2
(45) Date of Patent: Aug. 17, 2010

(54) ELECTRONIC BLOOD PRESSURE MONITOR AND DATA PROCESSING APPARATUS

(75) Inventors: Hiroshi Kishimoto, Kyoto (JP); Yukiya Sawanoi, Nara (JP); Kiichiro Miyata, Toyonaka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 513 days.

(21) Appl. No.: 11/501,830

(22) Filed: Aug. 10, 2006

(65) Prior Publication Data

US 2007/0038132 A1 Feb. 15, 2007

(30) Foreign Application Priority Data

Aug. 12, 2005 (JP) ............................. 2005-234870

(51) Int. Cl.
 *A61B 5/02* (2006.01)
(52) U.S. Cl. ................. 600/485; 600/500; 600/490; 600/495; 600/300
(58) Field of Classification Search ................. 600/500, 600/481, 485, 490, 493, 495, 300
See application file for complete search history.

(56) References Cited

U.S. PATENT DOCUMENTS

| | | | | |
|---|---|---|---|---|
| 4,995,399 | A * | 2/1991 | Hayashi et al. | 600/493 |
| 5,339,821 | A * | 8/1994 | Fujimoto | 600/513 |
| 5,649,536 | A | 7/1997 | Ogura et al. | |
| 6,699,195 | B2 * | 3/2004 | Nakazawa et al. | 600/485 |
| 7,018,335 | B2 * | 3/2006 | Kario et al. | 600/485 |
| 2004/0092831 | A1 | 5/2004 | Hood, Jr. | |
| 2004/0176692 | A1 * | 9/2004 | Kario et al. | 600/485 |

FOREIGN PATENT DOCUMENTS

| | | |
|---|---|---|
| DE | 19952715 | 6/2001 |
| DE | 103 53 096 | 7/2004 |
| EP | 0 356 016 | 2/1990 |
| EP | 1 421 898 | 5/2004 |
| EP | 1 568 313 A1 | 2/2005 |
| EP | 1 561 419 | 8/2005 |
| JP | 4-221528 A | 8/1992 |
| JP | 07088090 | 4/1995 |
| JP | 3020497 U | 1/1996 |
| RU | 9577 | 4/1999 |

OTHER PUBLICATIONS

European Search Report dated Jan. 3, 2007, directed to counterpart EP application No. 06016354.

(Continued)

*Primary Examiner*—Robert L Nasser
*Assistant Examiner*—Michael D'Angelo
(74) *Attorney, Agent, or Firm*—Morrison & Foerster LLP

(57) ABSTRACT

At the time of blood pressure measurement by an electronic blood pressure monitor, a calculation portion calculates a blood pressure based on a pressure within a cuff detected by a pressure sensor, and outputs blood pressure data. A data storing portion stores the blood pressure data in a memory in association with condition data indicating a condition concerning the blood pressure. A manipulation portion is manipulated by a user to designate a desired condition from among a plurality of conditions. When the manipulation portion is manipulated, a read and display portion searches the memory based on the condition designated by the manipulation, reads the blood pressure data associated with the designated condition from the memory, and displays the read data on a display portion.

15 Claims, 17 Drawing Sheets

OTHER PUBLICATIONS

Russian Decision on Grant mailed Mar. 31, 2008, directed to counterpart RU application No. 2006129228; 15 pages.

Russian Office Action dated Jun. 1, 2007, directed to counterpart RU application No. 2006129228/14.

* cited by examiner

ELECTRONIC BLOOD PRESSURE MONITOR AND DATA PROCESSING APPARATUS

BACKGROUND OF THE INVENTION

1. Field of the Invention

The present invention relates to an electronic blood pressure monitor and a data processing apparatus, and more particularly to an electronic blood pressure monitor and a data processing apparatus having functions of storing blood pressure measurement results in a memory and displaying the stored contents.

2. Description of the Background Art

In recent years, a blood pressure value is used as an index for health maintenance taking account of life-style related diseases attributable to high blood pressure, so that it is a critical issue how to manage the blood pressure measurement results. The blood pressure readily varies depending on the life environment or stress. Thus, trend management, with which the measured blood pressure values are managed in time series along with the measurement times, is useful, and blood pressure measurement enabling such trend management has been carried out.

For example, Japanese Utility Model Registration No. 3020497 discloses a digital automatic storage type blood pressure monitor, which has a memory content button at a push-button control circuit and allows a subject to use the memory content button to recall and display measurement data of previous measurements of several times.

Further, Japanese Patent Laying-Open No. 04-221528 discloses a device which specifies a blood pressure value, identification data, and measurement date and time, and selects and displays only the blood pressure values added with the identical identification data. It can also display a trend graph in accordance with the measurement situation.

With the blood pressure monitor disclosed in Japanese Utility Model Registration No. 3020497, although it has a large-capacity memory capable of storing large volume of measurement data, it only recalls the stored measurement values according to the stored order every time the memory content button is manipulated. As such, it is difficult to confirm the trend of the particular stored data. For example, as the morning hypertension has recently attracted attention, there is a demand for a function that can confirm only the blood pressure in the morning or the blood pressure in the evening. The device cannot fulfill such a demand.

In Japanese Patent Laying-Open No. 04-221528, separate keys are provided for setting conditions and for reading stored blood pressure data. It is thus difficult to intuitively understand the manipulation, resulting in poor usability.

SUMMARY OF THE INVENTION

An object of the present invention is to provide an electronic blood pressure monitor and a data processing apparatus excellent in manipulability in reading and displaying blood pressure data stored in association with conditions concerning the measured blood pressures, for each prescribed condition.

To achieve the above object, an electronic blood pressure monitor according to an aspect of the present invention includes: a blood pressure measurement unit having a cuff fitted to a blood pressure measurement site, a pressure increasing/decreasing unit adjusting a pressure applied to the cuff, a pressure detecting unit detecting a pressure within the cuff adjusted by the pressure increasing/decreasing unit, and a blood pressure calculation unit calculating a blood pressure based on the detected pressure by the pressure detecting unit; a memory; a display unit; a storing unit storing data of the blood pressure calculated by the blood pressure calculation unit in the memory in association with condition data indicating a condition concerning the blood pressure data; a manipulation unit manipulated for designating each of a plurality of such conditions; and a read and display unit, in response to manipulation of the manipulation unit, reading the blood pressure data associated with the condition data indicating the condition designated by the manipulation from the memory, and displaying the read blood pressure data on the display unit.

Accordingly, designation of the condition associated with the blood pressure data to be displayed on the display unit, and instruction to read the blood pressure data corresponding to the condition from the memory and display the read blood pressure data, can be given by manipulating the manipulation unit, without the need of conducting separate manipulations for designating the condition and for instructing the read and display.

Further, the subject can intuitively conduct the manipulation for reading the blood pressure data of the condition desired to be read and displayed from the memory and displaying the read blood pressure data.

Furthermore, the manipulation unit has switches for instructing reading of the blood pressure data and display of the read blood pressure data for the respective conditions. Thus, by simply manipulating the switch of a desired condition, it is possible to read and display only the blood pressure data satisfying the desired condition from the memory, without the need of performing condition setting.

Preferably, the condition indicates a condition at the time of blood pressure measurement by the blood pressure measurement unit.

Preferably, the electronic blood pressure monitor further includes a time-counting unit counting time, and the condition indicates the time of the blood pressure measurement counted by the time-counting unit.

Preferably, the storing unit stores, in the memory, data of the blood pressure calculated by the blood pressure calculation unit at the time of blood pressure measurement by the blood pressure measurement unit, in association with the condition data indicating the condition designated by manipulation of the manipulation unit at the time of the blood pressure measurement.

Accordingly, it is possible to use the manipulation unit for designating both of the condition to be associated with the blood pressure data obtained by measurement and the condition associated with the blood pressure data to be read from the memory for display.

Preferably, the condition is designated by manipulation of the manipulation unit, and reading of the blood pressure data from the memory is instructed by manipulation of the manipulation unit.

Accordingly, it is possible to use the manipulation unit both for instructing reading of the blood pressure data from the memory and for designating the condition.

Preferably, the storing unit stores, in the memory, data of the blood pressure calculated by the blood pressure calculation unit at the time of blood pressure measurement by the blood pressure measurement unit, in association with time data indicating a measurement time. The read and display unit reads the blood pressure data corresponding to the condition data indicating the designated condition from the memory in chronological sequence based on the time data associated with the blood pressure data, and displays the read blood pressure data on the display unit in accordance with the chronological sequence.

Accordingly, the blood pressure data associated with the designated condition are displayed in chronological sequence in accordance with the measurement times. This allows the subject to confirm the trend showing the changes of the blood pressure data over time.

Preferably, the memory has a plurality of memory areas corresponding to the plurality of conditions, respectively. The storing unit stores the blood pressure data calculated by the blood pressure calculation unit at the time of blood pressure measurement by the blood pressure measurement unit, in the memory area corresponding to the designated condition.

Accordingly, the blood pressure data is stored in the memory area corresponding to the designated condition, to be associated with the designated condition. When reading the blood pressure data from the memory, the blood pressure data may be read only from the memory area corresponding to the designated condition. This enables rapid data reading compared to the case of searching the entire memory to read data.

Preferably, the read and display unit has a comparison and notification unit comparing the blood pressure data read from the memory with reference blood pressure data, and notifying of a comparison result.

Preferably, the plurality of conditions include a condition indicating measurement after getting up and a condition indicating measurement before going to bed, or include a condition indicating measurement before meal and a condition indicating measurement after meal, or include a condition indicating measurement before exercise and a condition indicating measurement after exercise, or include a condition indicating measurement before medication and a condition indicating measurement after medication, or include a condition indicating measurement in the morning and a condition indicating measurement in the evening. Accordingly, it is possible to store, read and display the blood pressure data taking account of living habits that would cause considerable variation in blood pressure.

Preferably, the blood pressure calculation unit has an average calculation unit calculating weekly average data and/or monthly average data of the blood pressure data stored in the memory. The plurality of conditions include a condition indicating measurement of the weekly average and/or a condition indicating measurement of the monthly average.

Accordingly, at least one of the weekly average of blood pressure data and the monthly average of blood pressure data is stored in the memory in association with the condition (corresponding to at least one of the weekly average and the monthly average). It is thus possible to selectively read only the average data in association with the relevant condition from the memory and display the read average data.

A data processing apparatus according to another aspect of the present invention includes: a storing unit storing data of a blood pressure calculated with blood pressure measurement in a prepared memory in association with condition data indicating a condition concerning the blood pressure data; a manipulation unit manipulated for designating each of a plurality of such conditions; and a read and display unit, in response to manipulation of the manipulation unit, reading the blood pressure data associated with the condition data indicating the condition designated by the manipulation from the memory, and displaying the read blood pressure data on a prepared display unit.

A data processing method according to a further aspect of the present invention includes the steps of: storing data of a blood pressure calculated with blood pressure measurement in a prepared memory in association with condition data indicating a condition concerning the blood pressure data; inputting the condition data indicating the condition designated by manipulation; and reading from the memory, the blood pressure data associated with the input condition data and displaying the read blood pressure data on a prepared display unit.

A data processing apparatus according to yet another aspect of the present invention includes: a memory having data of a blood pressure calculated with blood pressure measurement stored in association with condition data indicating a condition concerning the blood pressure data; a manipulation unit manipulated for designating each of a plurality of such conditions; and a read and display unit, in response to manipulation of the manipulation unit, reading the blood pressure data associated with the condition data indicating the condition designated by the manipulation from the memory, and displaying the read data on a prepared display unit.

Preferably, the memory is detachable with respect to the data processing apparatus. Alternatively, the data processing apparatus further includes a communication unit, wherein the blood pressure data and the condition data received via a communication path by the communication unit are stored in the memory in association with each other.

Accordingly, when the blood pressure data measured by the electronic blood pressure monitor and the condition data to be associated therewith are applied to (stored in) the memory of an external data processing apparatus by a recording medium or via communication, the data can be read from the memory and displayed in the relevant data processing apparatus. Accordingly, the subject can confirm the blood pressure measurement result using the external data processing apparatus (other than the electronic blood pressure monitor).

According to the present invention, the subject can provide the apparatus with designation of the condition associated with the blood pressure data to be displayed on the display unit, and instruction to read the blood pressure data corresponding to the condition from the memory and display the read blood pressure data, by simply manipulating the manipulation unit. The subject does not need to perform separate manipulations for designating the condition and for instructing the read and display.

Further, the subject can intuitively perform the manipulation for reading the blood pressure data associated with a desired condition from the memory and displaying the read blood pressure data.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
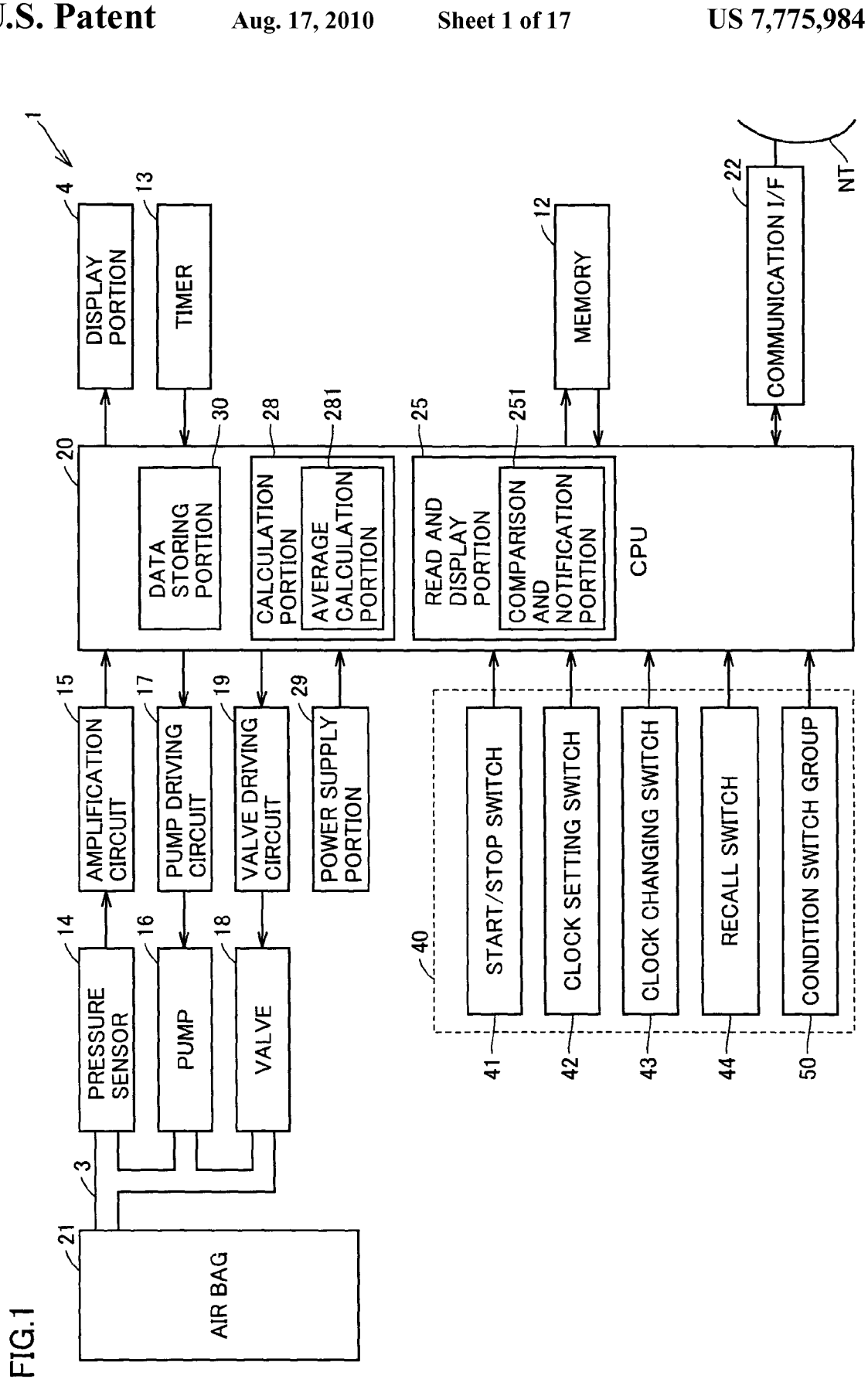
FIG. 1 is a functional configuration diagram of an electronic blood pressure monitor according to each embodiment.

Hereinafter, embodiments of the present invention will be described in detail with reference to the drawings. In the following, the same portions and components have the same reference characters allotted, and their designation and function are identical. Therefore, detailed description thereof will not be repeated.

(Configuration)

Figure 2:
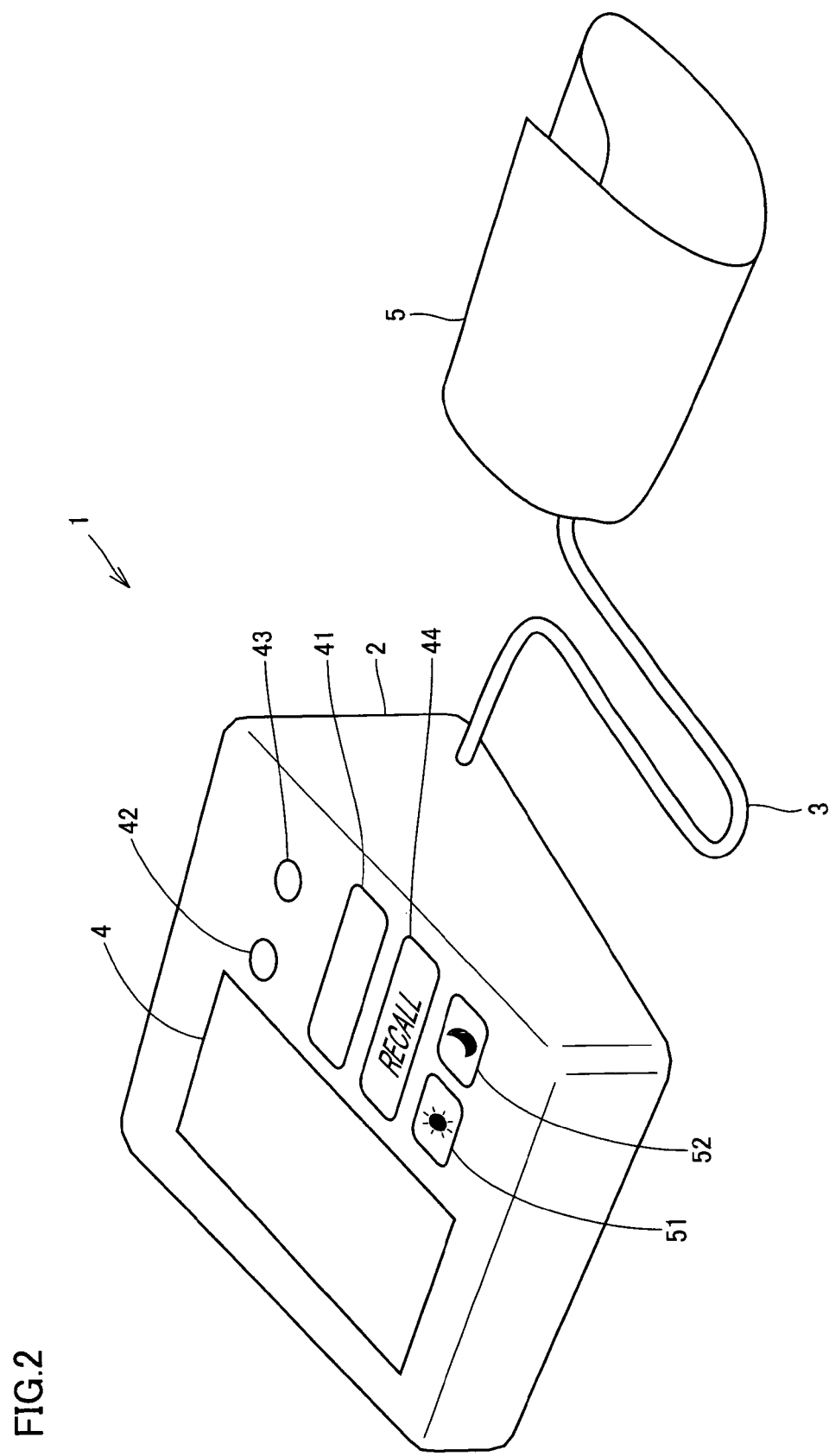
FIG. 2 is a general view of the electronic blood pressure monitor according to each embodiment.

A functional configuration of an electronic blood pressure monitor according to each embodiment is shown in FIG. 1, and its overview is shown in FIG. 2.

Referring to FIG. 2, an electronic blood pressure monitor 1 includes a cuff 5 fitted to a blood pressure measurement site of a subject and pressurized by an air pressure, and an air tube 3 connecting a blood pressure monitor main body 2 with cuff 5.

Blood pressure monitor main body 2 includes a display portion 4 provided for the subject to confirm a displayed content, a start/stop switch 41, a clock setting switch 42, a clock changing switch 43, a recall switch 44, a morning switch 51, and an evening switch 52 provided for the subject to be manipulable from the outside.

Start/stop switch 41 is manipulated to designate start and stop of blood pressure measurement. Clock setting switch 42 and clock changing switch 43 are manipulated to set and change the time of a timer 13, which will be described later, provided in electronic blood pressure monitor 1. Recall switch 44 is manipulated to designate (instruct) a series of operations (hereinafter, referred to as "recall") to read data designating a blood pressure measurement result stored in a memory from the memory, and display the read data on display portion 4. Morning switch 51 and evening switch 52 are manipulated to designate target data for recall when recalling the stored data of blood pressure measurement results. More specifically, morning switch 51 is manipulated to recall the result data of blood pressure measurement conducted in the morning time zone, and evening switch 52 is manipulated to recall the result data of blood pressure measurement conducted in the evening time zone.

Referring to FIG. 1, electronic blood pressure monitor 1 includes a pressure sensor 14 that outputs a change in pulse pressure at the measurement site detected via an air bag 21 contained in cuff 5 as a pulse wave signal, an amplification circuit 15 that amplifies a voltage signal indicating the pressure output from pressure sensor 14, a pump 16 and a valve 18 for adjusting a pressurizing (air pressure) level of air bag 21, a pump driving circuit 17 driving pump 16, a valve driving circuit 19 for adjusting opening/closing of valve 18, a display portion 4, a memory 12, a manipulation portion 40, a timer 13 serving as a time-counting portion that performs time-counting operation and outputs the time data, a communication I/F (Interface) 22, a power supply portion 29, and a CPU (Central Processing Unit) 20 that controls the respective portions.

Communication I/F 22 controls communication of electronic blood pressure monitor 1 with an external wired or wireless communication line NT. CPU 20 communicates with an external data processing apparatus 130, which will be described later, via communication I/F 22 and communication line NT. For example, CPU 20 transmits data of blood pressure measurement results read from memory 12 to data processing apparatus 130 via communication I/F 22 and communication line NT.

CPU 20 has, therein, a memory (not shown) for temporarily storing data, a read and display portion 25, a calculation portion 28 calculating blood pressure and pulsation, and a data storing portion 30 having a function of storing blood pressure measurement data in memory 12. CPU 20 has a function of processing the blood pressure measurement data. Read and display portion 25 controls display on display portion 4. The functions of read and display portion 25, calculation portion 28, and data storing portion 30 are realized as CPU 20 reads and executes a prescribed program from memory 12. Calculation portion 28 includes an average calculation portion 281 that calculates an average of the blood pressure measurement data. It is noted that memory 12 may be formed of a partial memory storing various programs and data controlling the operation of electronic blood pressure monitor 1 and a partial memory storing the blood pressure measurement data, and the partial memory storing the blood pressure measurement data may be provided to electronic blood pressure monitor 1 in a detachable manner. Further, display portion 4 may be provided to electronic blood pressure monitor 1 in a detachable manner as well. In such a case, at the time of blood pressure measurement and at the time of recalling the measurement data, these portions are attached to electronic blood pressure monitor 1 in advance.

Air bag 21 is connected to pressure sensor 14, pump 16 and valve 18 via air tube 3. Herein, power supply portion 29, supplying power for driving the respective portions, is formed of a battery or a commercial power source. Calculation portion 28 calculates a blood pressure value, a pulse rate and the like based on the pulse signal input from amplification circuit 15.

Manipulation portion 40 has the switches shown in FIG. 2, including start/stop switch 41, clock setting switch 42 and clock changing switch 43 for setting the time of timer 13, recall switch 44, and a condition switch group 50. Condition switch group 50 has a plurality of switches corresponding to respective measurement conditions, which are manipulated to designate the corresponding blood pressure measurement conditions. Morning switch 51 and evening switch 52 are included in condition switch group 50.

Memory 12 stores various data including the measurement result data, and various programs.

In the above-described configuration, at the time of blood pressure measurement, calculation portion 28 converts the pulse signal (pressure signal) output from amplification circuit 15 to digital data, and then applies a prescribed algorithm to the data to calculate a systolic blood pressure (maximum blood pressure), a diastolic blood pressure (minimum blood pressure), and a pulse rate. Known procedures can be used for such calculation, and thus, detailed description thereof is not provided here.

First Embodiment

A blood pressure measurement operation using electronic blood pressure monitor 1 will now be described with reference to the flowchart of FIG. 3. Each flowchart described hereinafter, including the flowchart of FIG. 3, is pre-stored in memory 12 as a program, and read and executed by CPU 20.

Figure 3:
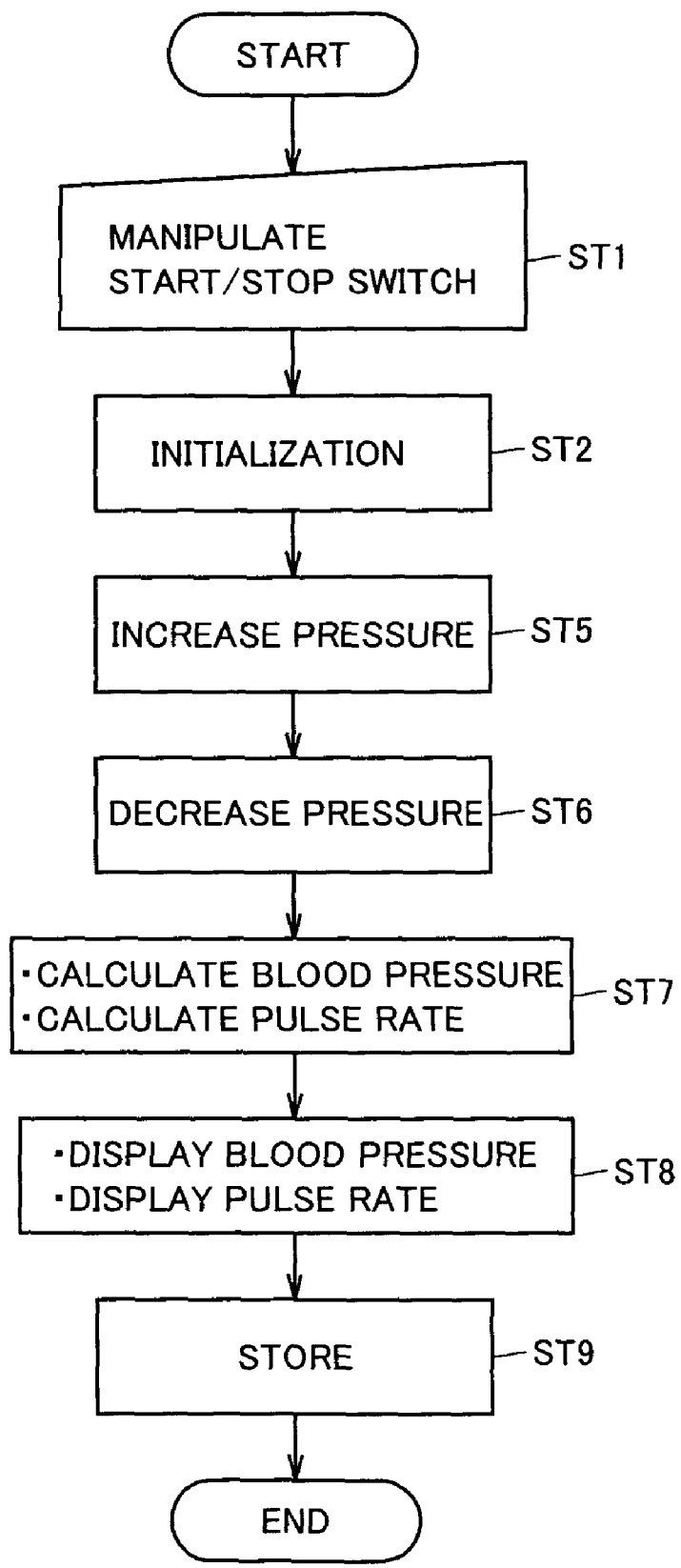
FIG. 3 is a flowchart of blood pressure measurement according to a first embodiment.

Referring to FIG. 3, firstly, when a subject winds cuff 5 around the measurement site (upper arm, wrist, finger or the like) and manipulates start/stop switch 41 of electronic blood pressure monitor 1, a manipulation signal is applied to CPU 20. CPU 20, in response to the applied manipulation signal, controls power supply portion 29 to start power supply to the respective portions (step ST (hereinafter, simply referred to as "ST") 1). Next, as the initialization processing of electronic blood pressure monitor 1, CPU 20 controls certain portions to evacuate the air within air bag 21 such that the output level of pressure sensor 14 is 0 mmHg (ST2).

Next, CPU 20 controls certain portions to increase the pressure within air bag 21 to about the systolic blood pressure of the subject+40 mmHg (ST5), and then gradually decreases the pressure within air bag 21 (ST6). During this pressure-decreasing process, the pressure within air bag 21 is detected by pressure sensor 14. Calculation portion 28 of CPU 20 calculates the (systolic and diastolic) blood pressure values and the pulse rate based on the detected pressure, and temporarily stores them in an internal memory of CPU 20 (ST7). Read and display portion 25 displays the calculated blood pressure values and pulse rate on display portion 4 (ST8). The pressure increasing and decreasing processes for the blood pressure measurement are similar to those of a conventional electronic blood pressure monitor. Although it is herein configured to measure the blood pressure during the pressure-decreasing process, it may be measured during the pressure-increasing process.

When the calculation and display of the blood pressure and pulsation are finished, data storing portion 30 of CPU 20 reads the measurement results (data of systolic blood pressure, diastolic blood pressure and pulse rate) temporarily stored in the internal memory, and stores the read measurement result data in memory 12 in association with the time data counted by timer 13 as the measurement time data (ST9). A series of blood pressure measurement operations are thus completed.

Figure 6:
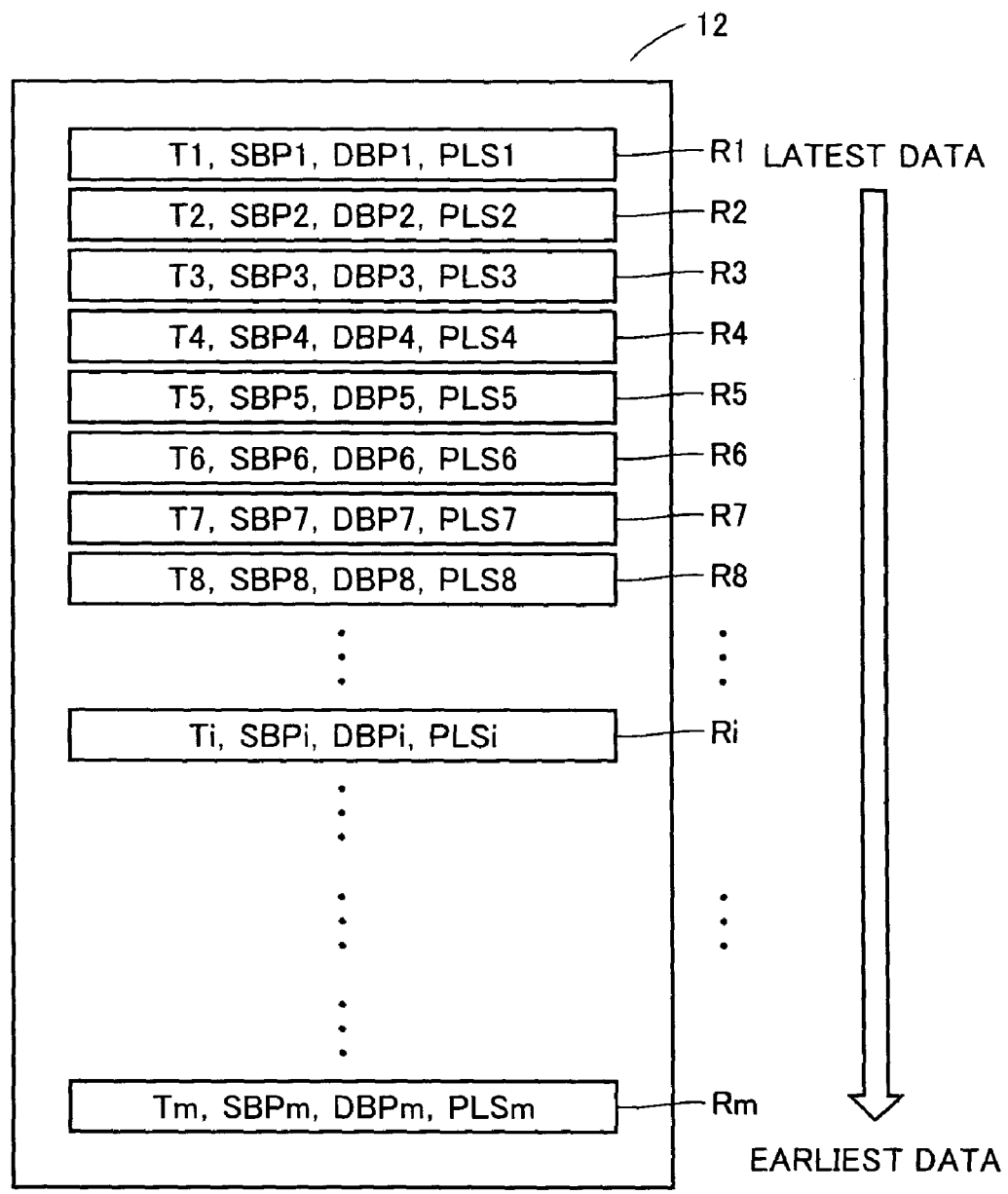
FIG. 6 shows a data storage example according to the first embodiment

In the present embodiment, the blood pressure measurement result data in ST9 of FIG. 3 is stored in memory 12 as shown in FIG. 6.

In FIG. 6, the measurement results are stored in memory 12 in units of records Ri (i=1, 2, . . . , m). Record Ri includes measurement time data Ti, systolic blood pressure data SBPi indicating the systolic blood pressure, diastolic blood pressure data DBPi indicating the diastolic blood pressure, and pulse rate data PLSi indicating the pulse rate. The storage manner of the data is not restricted to the one using records Ri. All that is needed is that each time measurement is carried out, the data are stored in memory 12 in an associated manner such that the correspondence of the measurement values with the measurement can be specified.

For measurement time data Ti, CPU 20 receives data of the time when the blood pressure was measured (i.e., time of start or end of measurement) counted by timer 13 and converts it to measurement time data Ti (year, month, day, hour, minute), which is stored in record Ri. As such, measurement time data Ti indicates a measurement condition concerning the corresponding systolic blood pressure data SBPi and diastolic blood pressure data DBPi. In FIG. 6, records Ri are stored in memory 12 in chronological sequence of measurement times, from the latest data (measured most recently) to the earliest data (measured most previously).

Hereinafter, procedure of recalling record Ri in memory 12 will be described. Herein, it is assumed that a sufficient number of records Ri over all the time of day are stored in memory 12.

Figure 4:
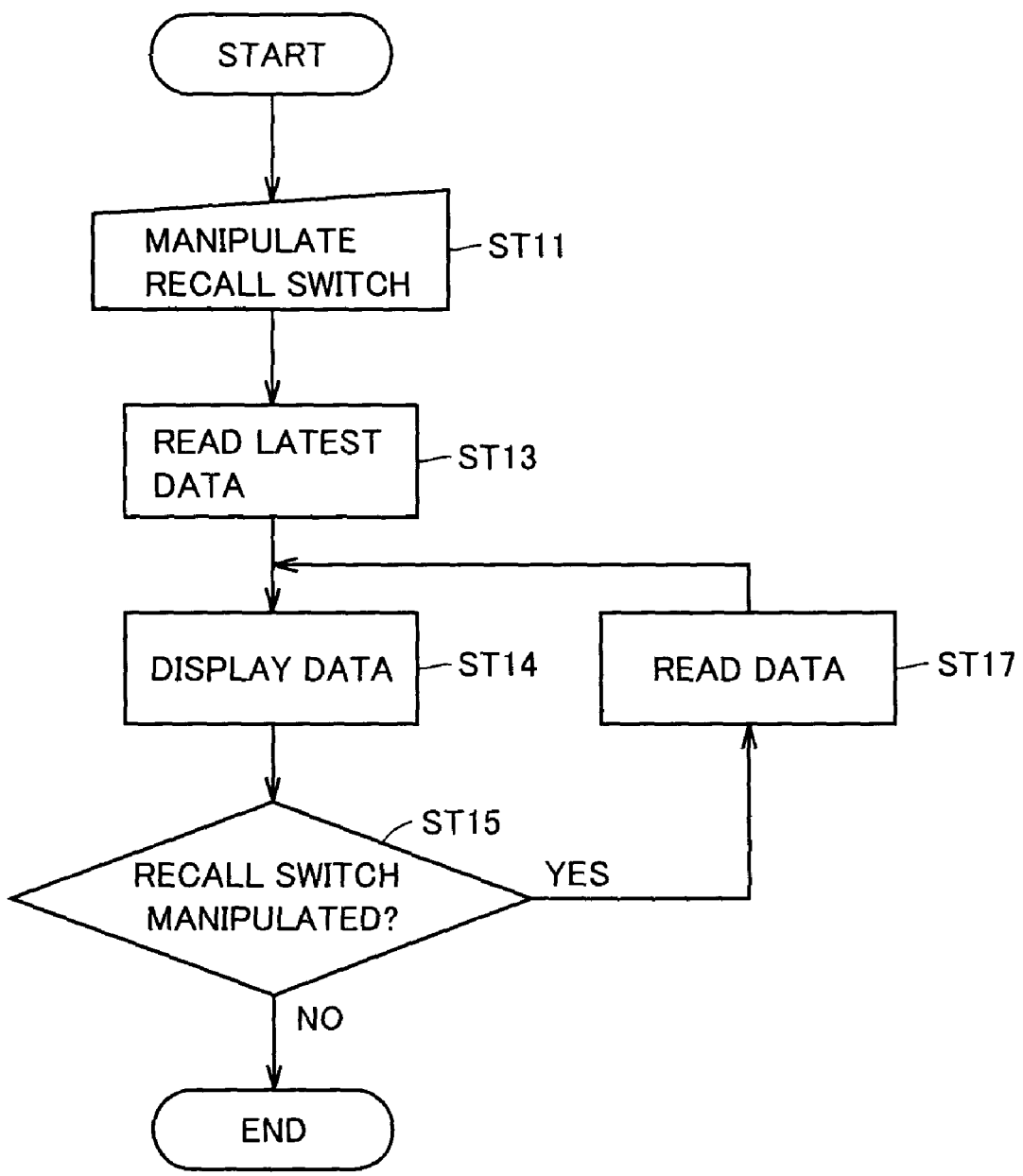
FIG. 4 is a flowchart illustrating an example of recall procedure according to the first embodiment.

The procedure of recalling the blood pressure measurement data in memory 12 in order from the latest to the earliest is shown in FIG. 4.

Firstly, the subject manipulates recall switch 44 (ST11). In response to the manipulation signal, read and display portion 25 of CPU 20 conducts the following operations. It starts reading of record Ri stored most recently (e.g., record Ri registered at a leading address in an area for registration of records Ri in memory 12) from memory 12 (ST13). It then displays the measurement result on display portion 4 based on the content of the read record Ri (ST14). Thereafter, if there is no manipulation of recall switch 44 by the subject (NO in ST15), the process is finished. If there is a manipulation (YES in ST15), read and display portion 25 retrieves and reads next latest record Ri (or record Ri stored in the next address) from among records Ri in memory 12 (ST17), and displays data on display portion 4 based on the content of the read record Ri (ST14). It then moves to ST15. The loop processing of ST17, ST14 and ST15 is carried out repeatedly every time recall switch 44 is manipulated. As a result, records Ri are read from memory 12 in FIG. 6 from the latest one to the earliest one, i.e., sequentially from the leading record Ri in memory 12, and their contents are displayed. Herein, the order of records Ri from the latest to the earliest is specified by following the order of registration (storage) of records Ri, i.e., the order of measurement. Alternatively, the order of records Ri from the latest to the earliest may be specified by ordering records Ri with reference to time data Ti.

Procedure of recalling blood pressure measurement data measured in the morning from memory 12 in order from the latest to the earliest will now be described with reference to FIG. 5.

Firstly, the subject manipulates morning switch 51 (ST18). In response to a signal based on the manipulation, read and display portion 25 of CPU 20 conducts the following operations. It reads from memory 12 record Ri that was stored most recently (ST19). It determines whether time data Ti of the read record Ri indicates any time from 4:00 am to 10:00 am (ST20), and if not (NO in ST20), it reads the next latest record Ri from memory 12 (ST23), and performs determination of ST20. It is assumed that the data indicating the time from 4:00 am to 10:00 am for use in determination of ST20 is stored in advance in memory 12 or incorporated in the logic of the program, or input by the subject.

Meanwhile, if read and display portion 25 determines that time data Ti of record Ri indicates any time from 4:00 am to 10:00 am (YES in ST20), it moves to ST21 and displays the measurement result on display portion 4 based on the content of the relevant record Ri (ST21). Thereafter, if morning switch 51 is not manipulated by the subject (NO in ST22), the process is terminated. If the switch is manipulated (YES in ST22), it reads the next latest data from memory 12 (ST23). Thereafter, the processing in and after ST20 are repeated in a similar manner.

As such, the loop processing of ST20 through ST23 is repeatedly executed every time morning switch 51 is manipulated, and records Ri storing the measurement result data corresponding to the designated condition of the blood pressure measured in the morning are read from memory 12 in order from the latest to the earliest, and the contents of the read records Ri are displayed.

Figure 7:
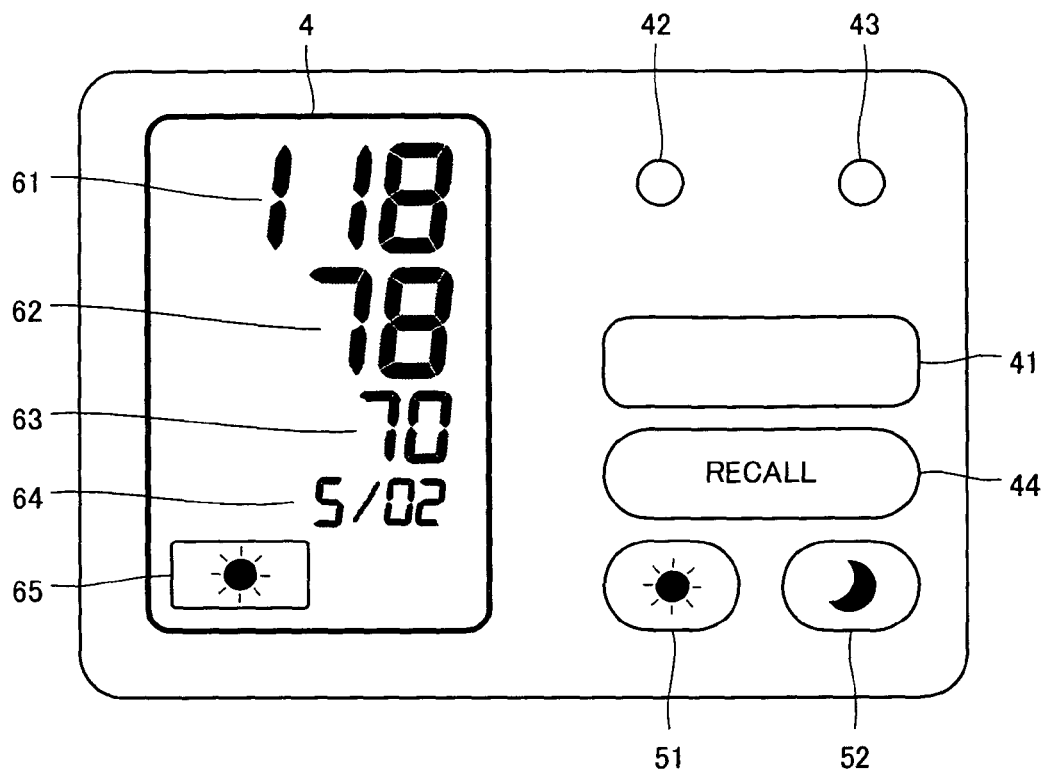
FIG. 7 shows an example of data display according to the first embodiment.

FIG. 7 shows a display example of record Ri in ST21. In FIG. 7, systolic blood pressure data 61 based on systolic blood pressure data SBPi, diastolic blood pressure data 62 based on diastolic blood pressure data DBPi, pulse rate data 63 based on pulse rate data PLSi, and time data 64 based on measurement time data Ti are displayed on display portion 4. A mark 65 for designating the condition that the measurement result data being displayed corresponds to one measured in the morning time zone is also displayed. For time data 64, month and date, and hour and minute, are displayed alternately in the same segment.

The display in accordance with the procedure of FIG. 4 is similar to that shown in FIG. 7, except that there is no display of mark 65, and that data 61-64 indicate the measurement result data of record Ri read in order from the latest to the earliest.

Figure 5:
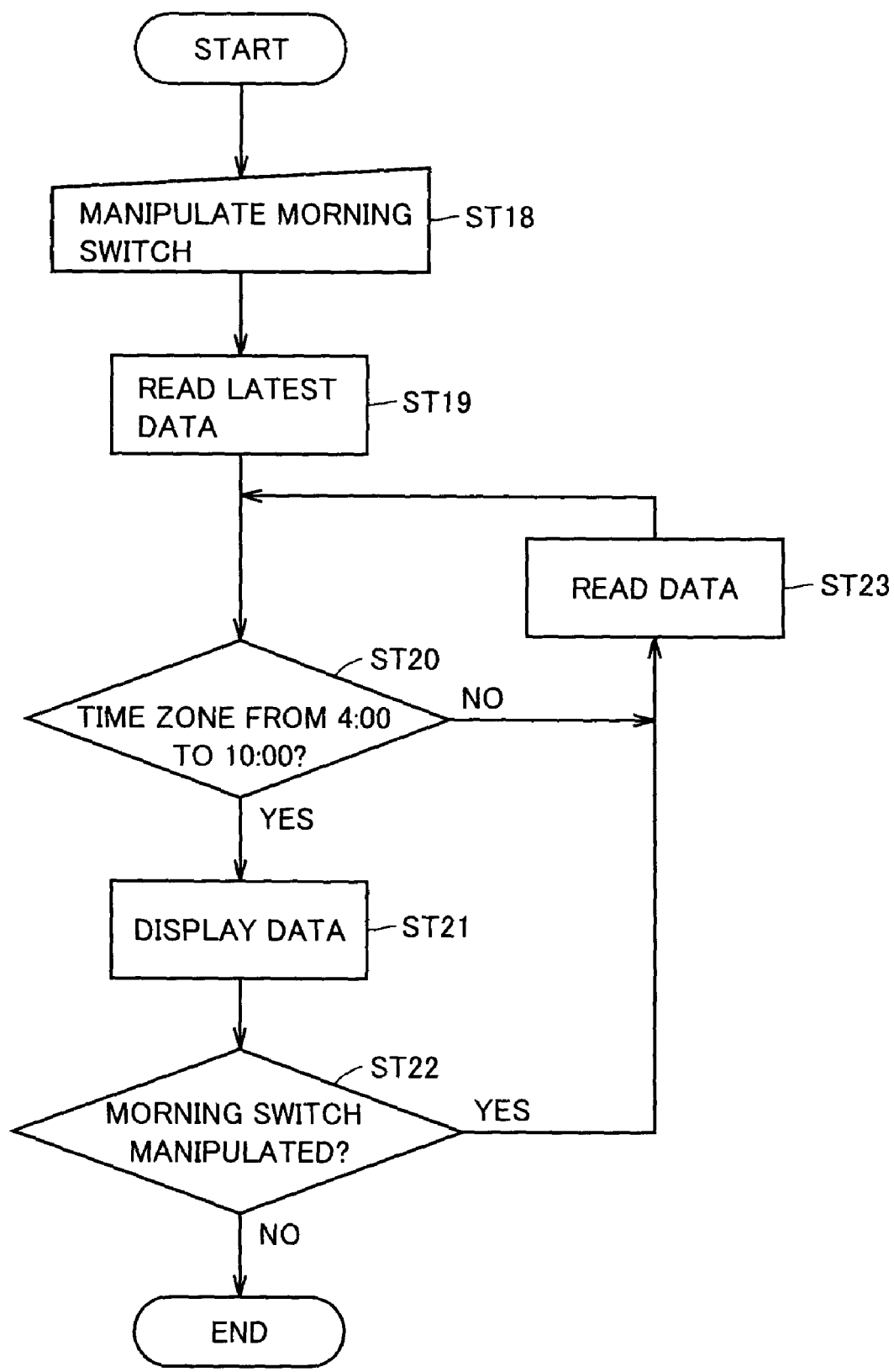
FIG. 5 is a flowchart illustrating another example of recall procedure according to the first embodiment.
Figure 8:
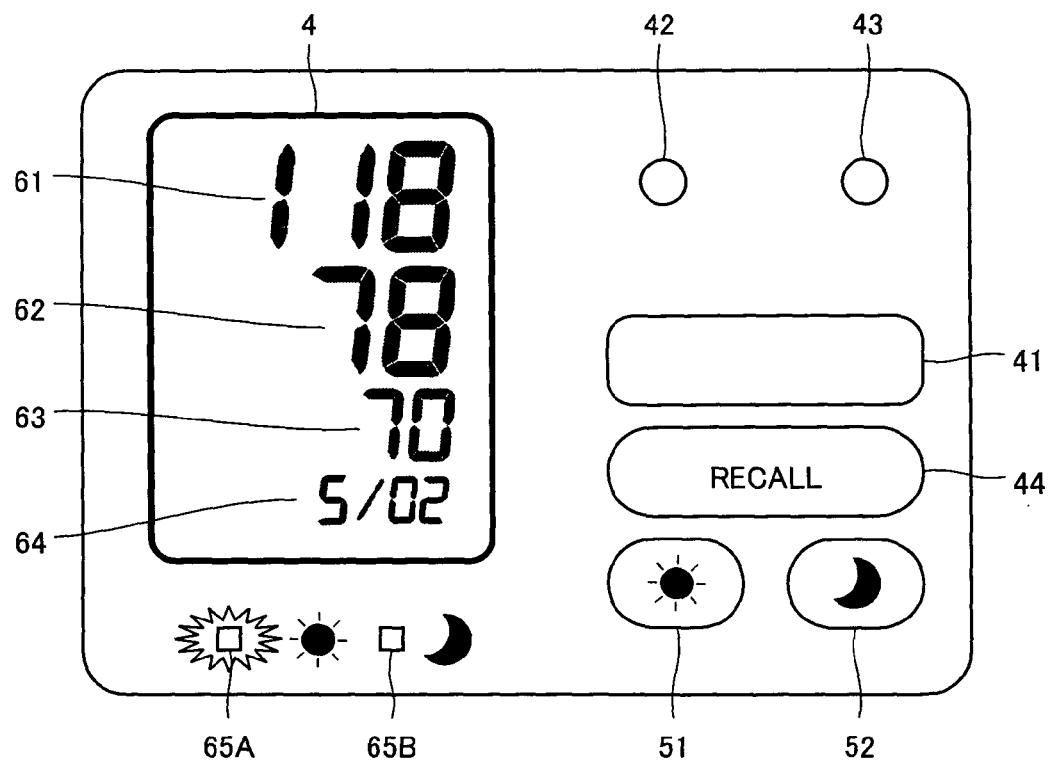
FIG. 8 shows another example of data display according to the first embodiment.

The display example according to the procedure of FIG. 5 is not restricted to the one shown in FIG. 7, but may be as shown in FIG. 8. In FIG. 8, in place of mark 65 in FIG. 7, LED (Light Emitting Diodes) 65A and 65B for morning and evening, respectively, are provided. Read and display portion 25 may be configured to turn on one of LED 65A and 65B in accordance with the measurement condition (whether morning or evening) of the blood pressure measurement data being displayed. In FIG. 8, LED 65A is on and LED 65B is off, in response to the manipulation of morning switch 51. This indicates that the condition upon measurement of the blood pressure data now on display is measurement in the morning.

Figure 9:
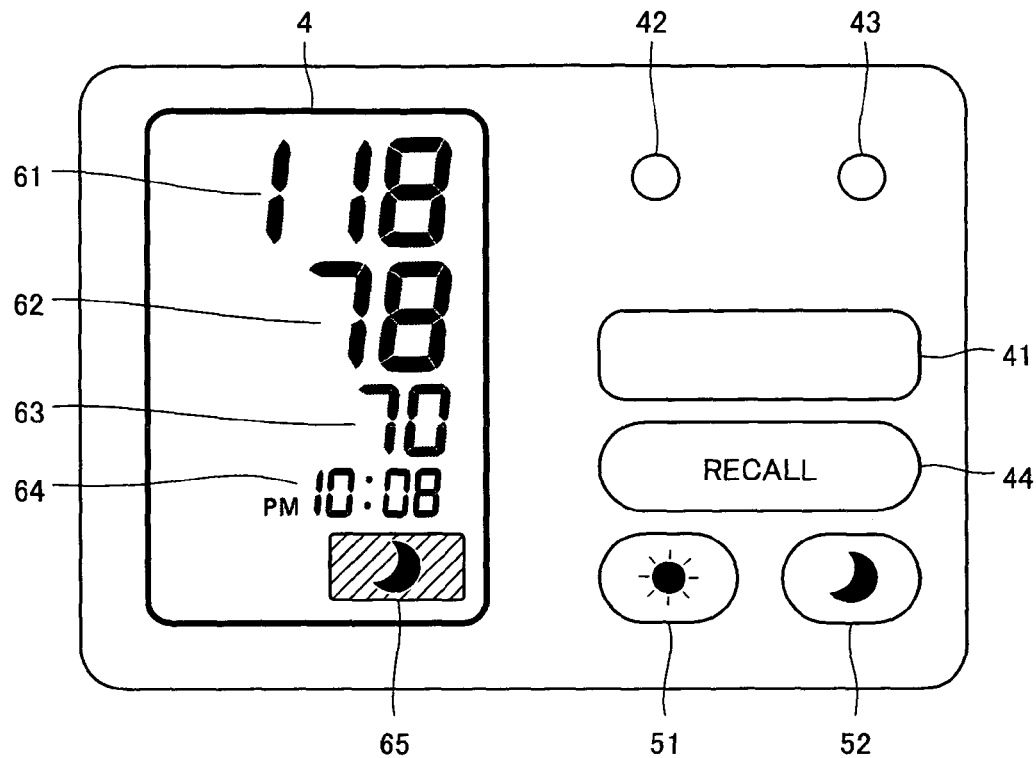
FIG. 9 shows yet another example of data display according to the first embodiment.
Figure 10:
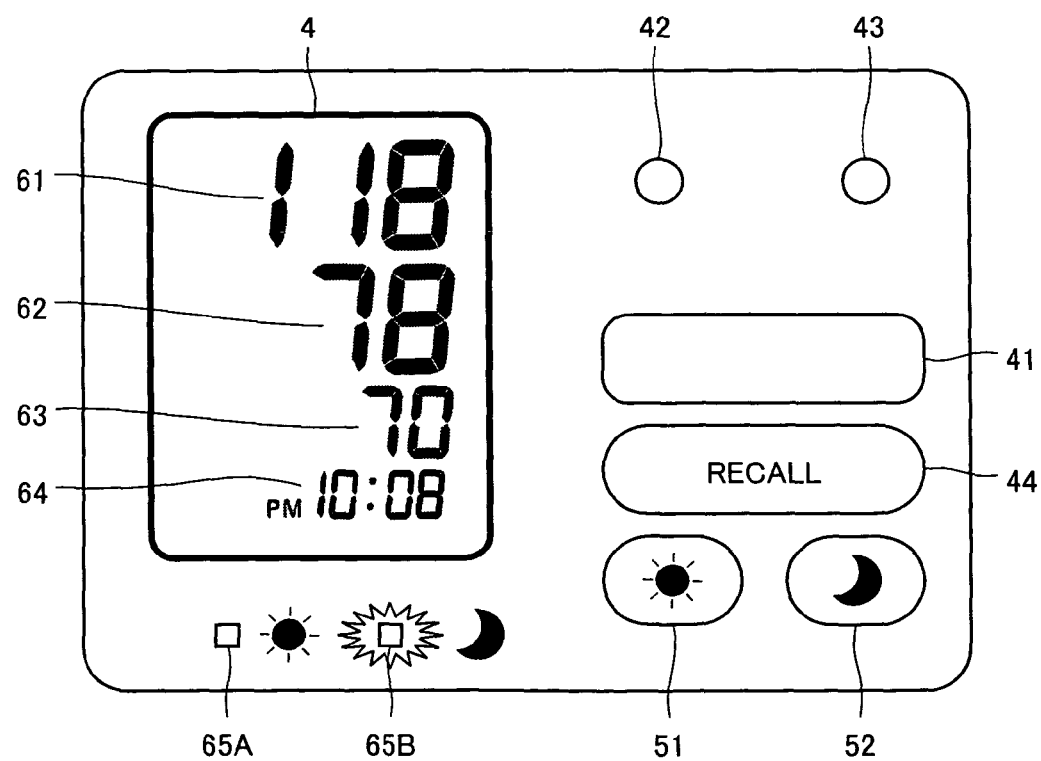
FIG. 10 shows a further example of data display according to the first embodiment.

In the procedure of FIG. 5, the measurement result data satisfying the condition of measurement in the morning are recalled sequentially every time morning switch 51 is manipulated in ST18 or ST22. Alternatively, it may be configured to recall the measurement result data corresponding to the condition of measurement in the evening every time evening switch 52 is manipulated instead of morning switch 51. In this case, the data indicating the time zone from 4:00 pm to 4:00 am is referred to for the determination in ST20. Further, the display is as shown in FIGS. 9 and 10. In the display of FIG. 9, mark 65 shown in FIG. 7 is changed to indicate that the condition is measurement in the evening. In the display of FIG. 10, LED 65A is off and LED 65B is on to indicate the condition of measurement in the evening.

Second Embodiment

In the present embodiment, the recalled measurement blood pressure data is compared with prescribed reference blood pressure data, and the result of comparison is notified.

Figure 11:
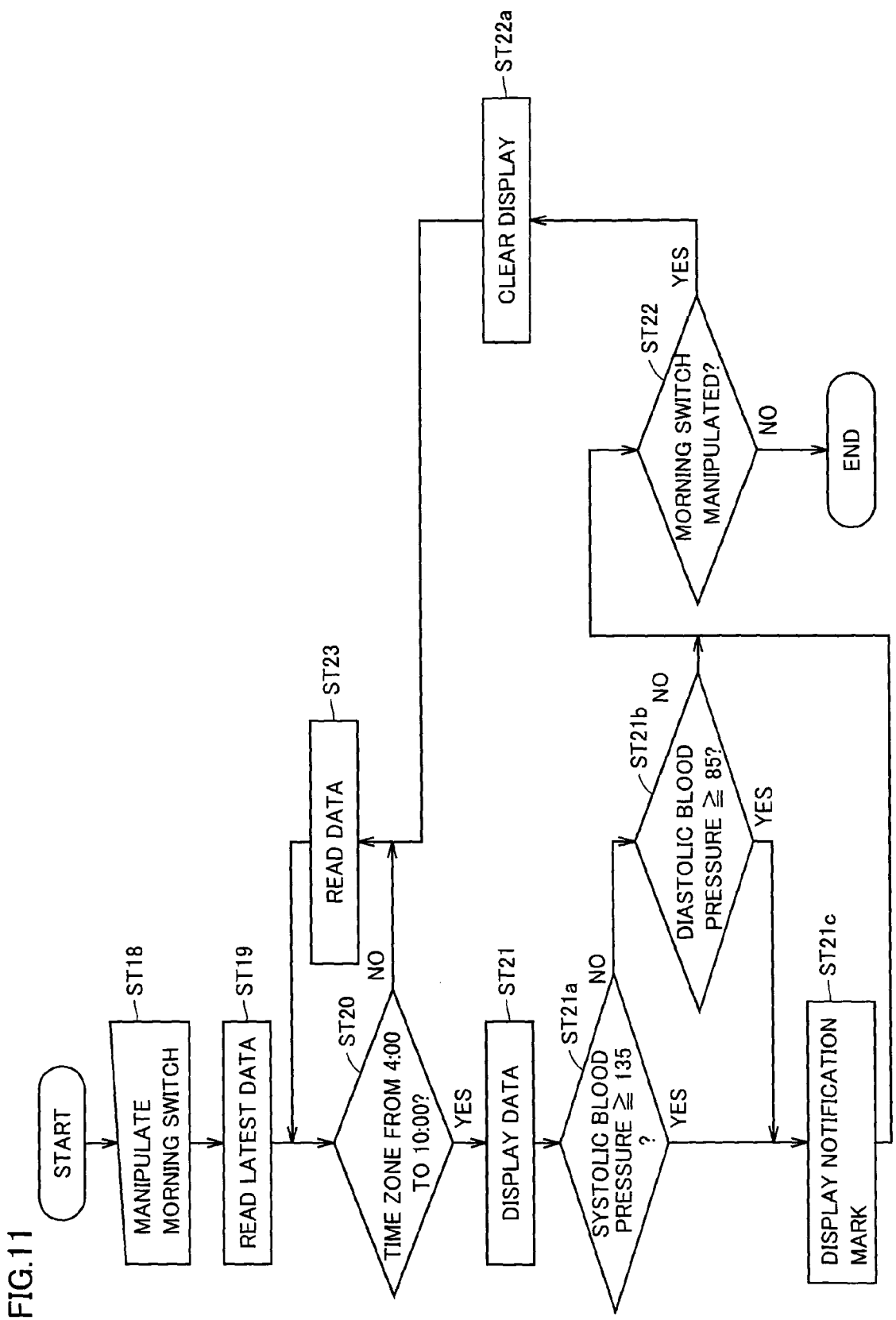
FIG. 11 is a flowchart illustrating an example of recall procedure according to a second embodiment.

FIG. 11 shows procedure for recalling measurement data according to the present embodiment. The procedure in FIG. 11 corresponds to the procedure in FIG. 5 to which processing for the above-mentioned comparison (ST21a, ST21b), processing of notifying of the result of comparison (ST21c), and processing of clearing the display (ST22a) are added. Thus, the added processing will now be described in detail.

Figure 12:
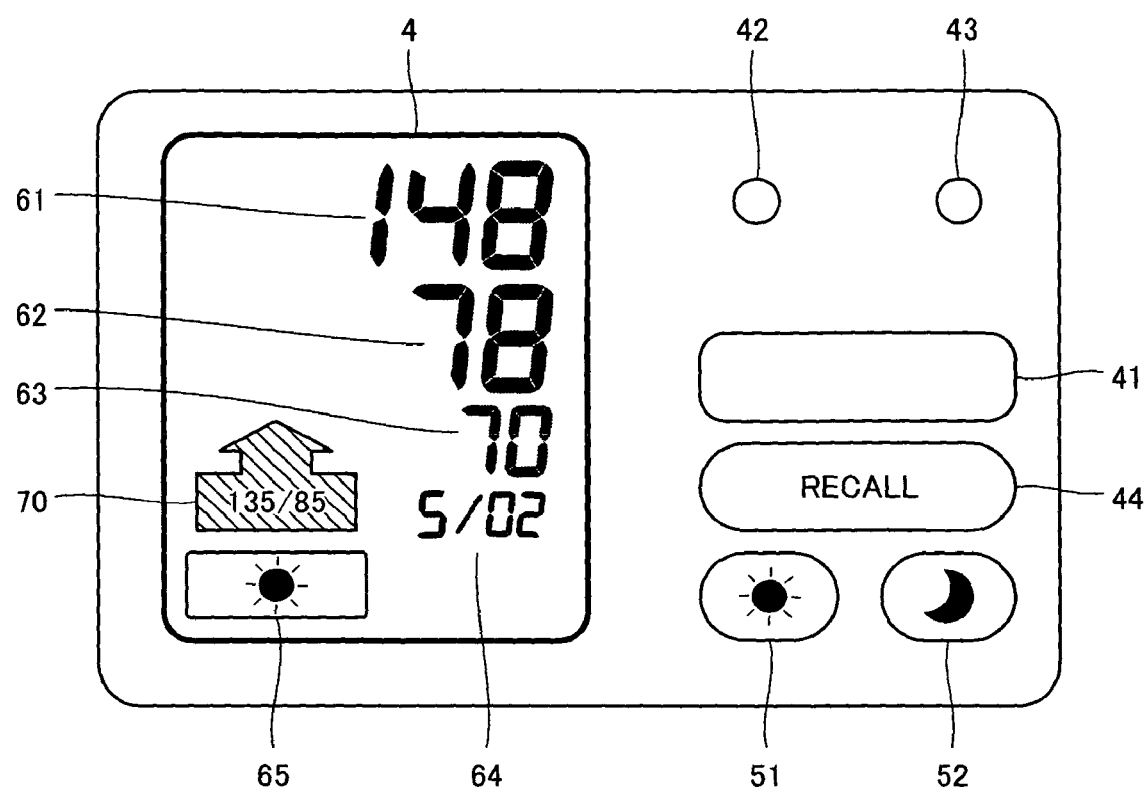
FIG. 12 shows an example of data display according to the second embodiment.

The processing in ST18 through ST20 are carried out in a similar manner as described above, and in next ST21, measurement result data is displayed on display portion 4 based on the content of the read record Ri. A comparison and notification portion 251 of read and display portion 25 compares the blood pressure values indicated by systolic blood pressure data 61 (read systolic blood pressure data SBPi) and diastolic blood pressure data 62 (read diastolic blood pressure data DBPi) now being displayed with prescribed reference values (reference value of 135 mmHg for the systolic blood pressure, and reference value of 85 mmHg for the diastolic blood pressure) (ST21a, ST21b). It then displays a notification mark based on the result of comparison, as shown in FIG. 12 (ST21c). In FIG. 12, a notification mark 70 is displayed in addition to the display data of FIG. 7. It is noted that the reference values (135 mmHg for the systolic blood pressure and 85 mmHg for the diastolic blood pressure) are defined, e.g., by Joint National Committee on Prevention, Detection, Evaluation, and Treatment of High blood Pressure in the U.S.A., or by Japanese Society of Hypertension as the reference values of home blood pressure for determination of high blood pressure. They are pre-stored in an internal memory (not shown) in CPU 20, or incorporated in the logic of the flowchart in FIG. 11.

If comparison and notification portion 251 determines that the comparison relation (condition) of [systolic blood pressure≧135 mmHg] or [diastolic blood pressure≧85 mmHg] is satisfied (YES in ST21a or YES in ST21b), it displays notification mark 70.

After display of the notification mark (ST21c), or if it is determined that the comparison relations (conditions) of [systolic blood pressure≧135 mmHg] and [diastolic blood pressure≧85 mmHg] are not satisfied (NO in ST21a and NO in ST21b), it is determined in ST22 whether morning switch 51 has been manipulated. If so (YES in ST22), read and display portion 25 clears the display content on display portion 4. More specifically, it erases the display data on display portion 4, turns off LED 65A and 65B (ST22a), and proceeds to processing in ST23.

Although notification mark 70 has been configured to be displayed (lighted) when the above comparison relation is satisfied, it may be blinked instead. Further, mark 65 may be used also as the notification mark, without provision of notification mark 70. That is, mark 65 may be blinked when the above comparison relation is satisfied. Furthermore, lighting of an LED, vibration of electronic blood pressure monitor 1, or a sound may be used for notification.

Third Embodiment

Figure 13:
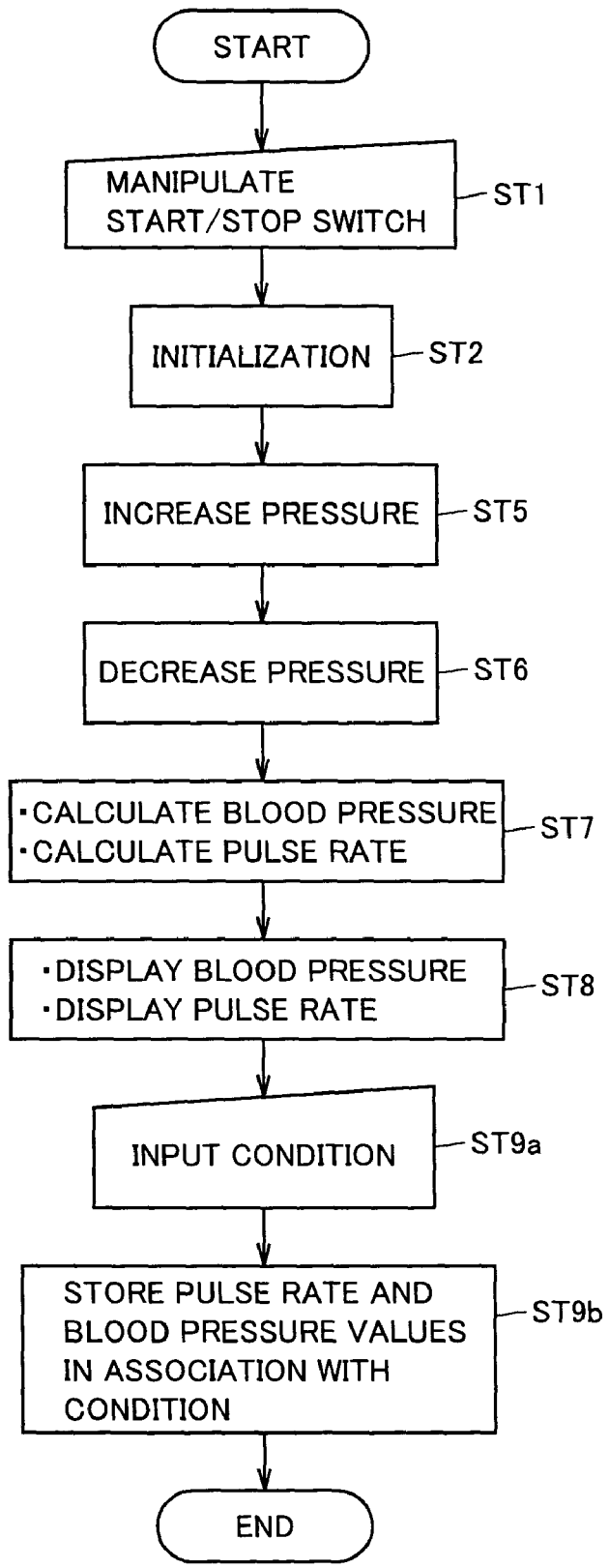
FIG. 13 is a flowchart of blood pressure measurement according to a third embodiment.
Figure 14:
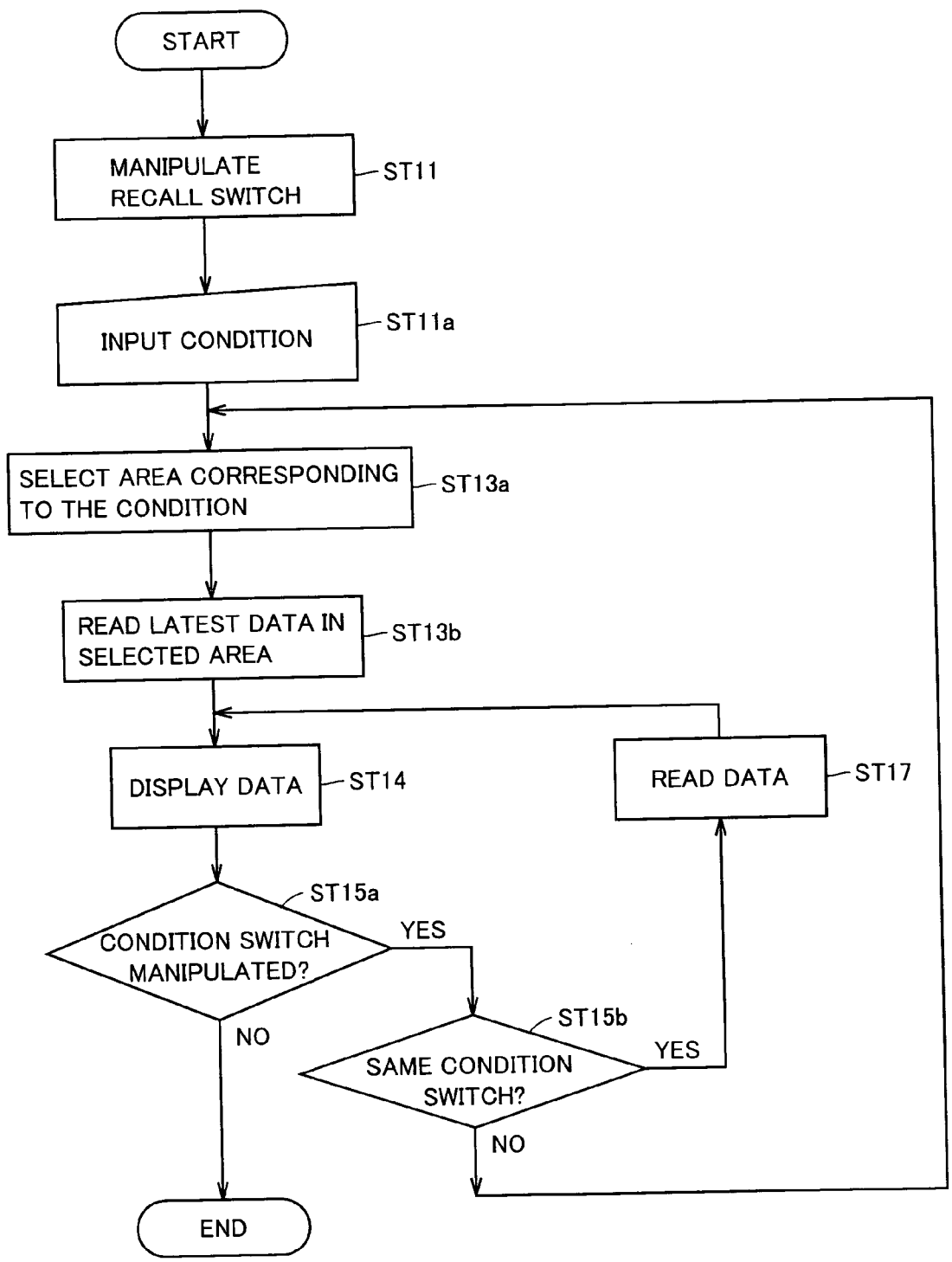
FIG. 14 is a flowchart illustrating an example of recall procedure according to the third embodiment.

In the present embodiment, a manipulation of designating a condition concerning the blood pressure being measured is conducted at the time of blood pressure measurement, as shown in the flowchart of FIG. 13, and measurement result data (record Ri) is stored in memory 12 in association with the condition. At the time of recalling, a manipulation of designating the condition is conducted, as shown in the flowchart of FIG. 14, and the measurement result data is recalled from an area in memory 12 corresponding to the designated condition. Content examples of memory 12 in the present embodiment are shown in FIGS. 15A and 15B.

Herein, the conditions indicate prescribed measurement time zones based on living habits, such as after getting up, before going to bed, before meal, after meal, before exercise, after exercise, and the like, although they are not restricted thereto. For example, they may indicate prescribed time zones such as before medication, after medication and the like. It is assumed that the length of a prescribed time zone is predetermined, for example two hours after getting up (two hours before going to bed) for determination of the morning hypertension.

Figure 16:
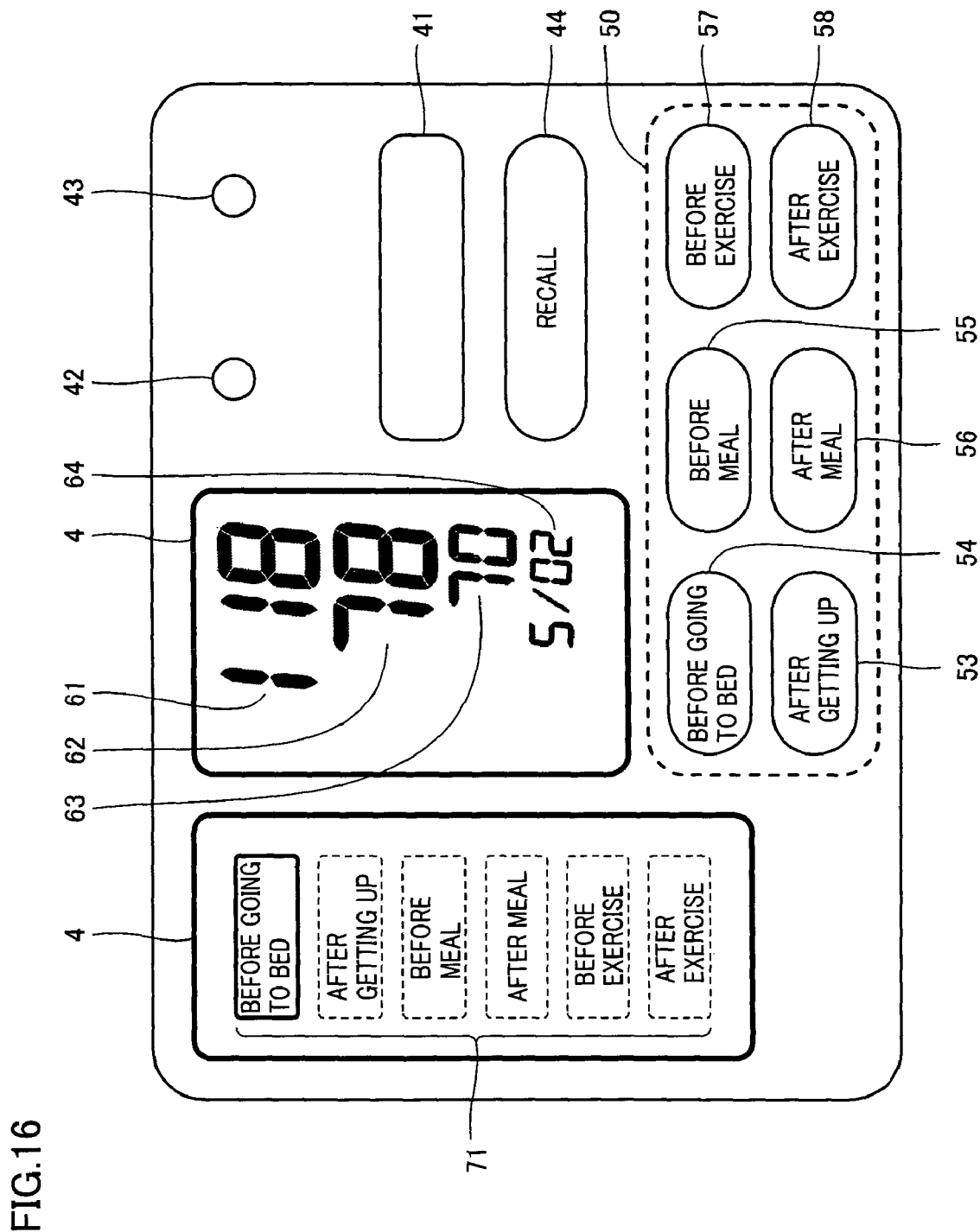
FIG. 16 shows a data display example and a condition switch group according to the third embodiment.

In the present embodiment, as shown in FIG. 16, condition switch group 50 includes condition switches 53-58 provided corresponding to the respective measurement conditions of after getting up, before going to bed, before meal, after meal, before exercise, and after exercise. At the time of measurement of blood pressure, the subject can manipulate a switch in condition switch group 50 corresponding to the desired measurement condition. In doing so, the subject can designate the condition that is to be associated with the measurement result data at the time of storing the relevant blood pressure measurement result data in memory 12. At the time of recalling the blood pressure measurement result data, the subject can designate the condition associated with the blood pressure measurement result data to be recalled, by manipulating the switch in condition switch group 50 corresponding to the desired measurement condition.

Figure 15B:
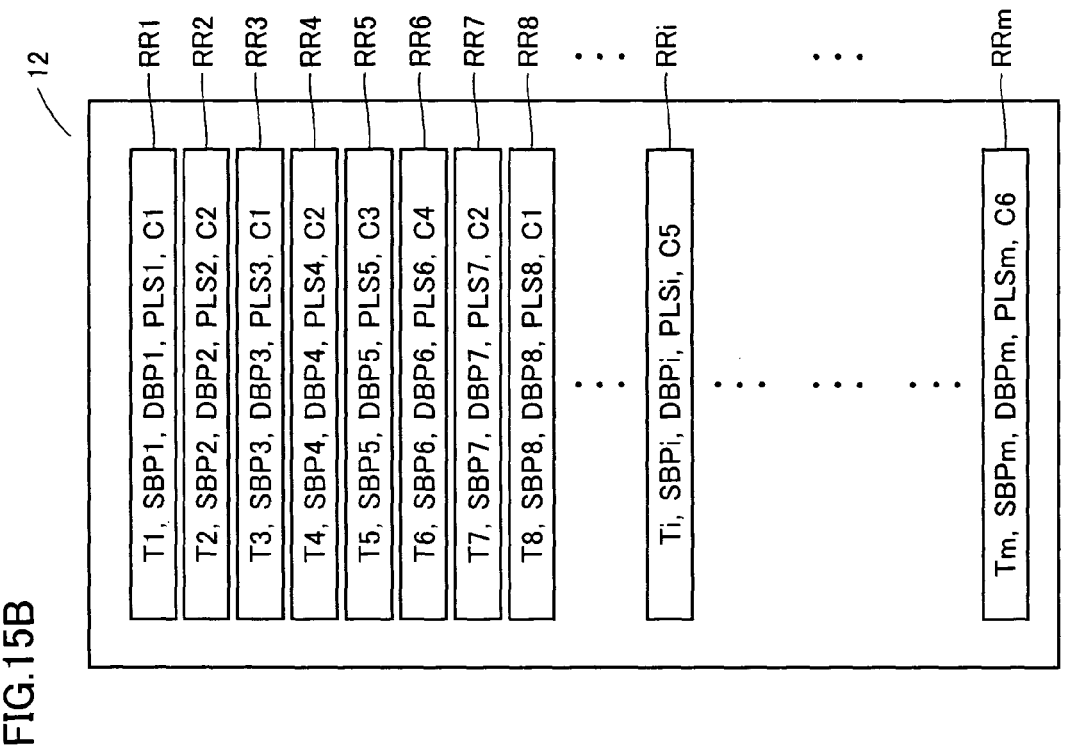
FIGS. 15A and 15B show data storage examples according to the third embodiment.
Figure 15A:
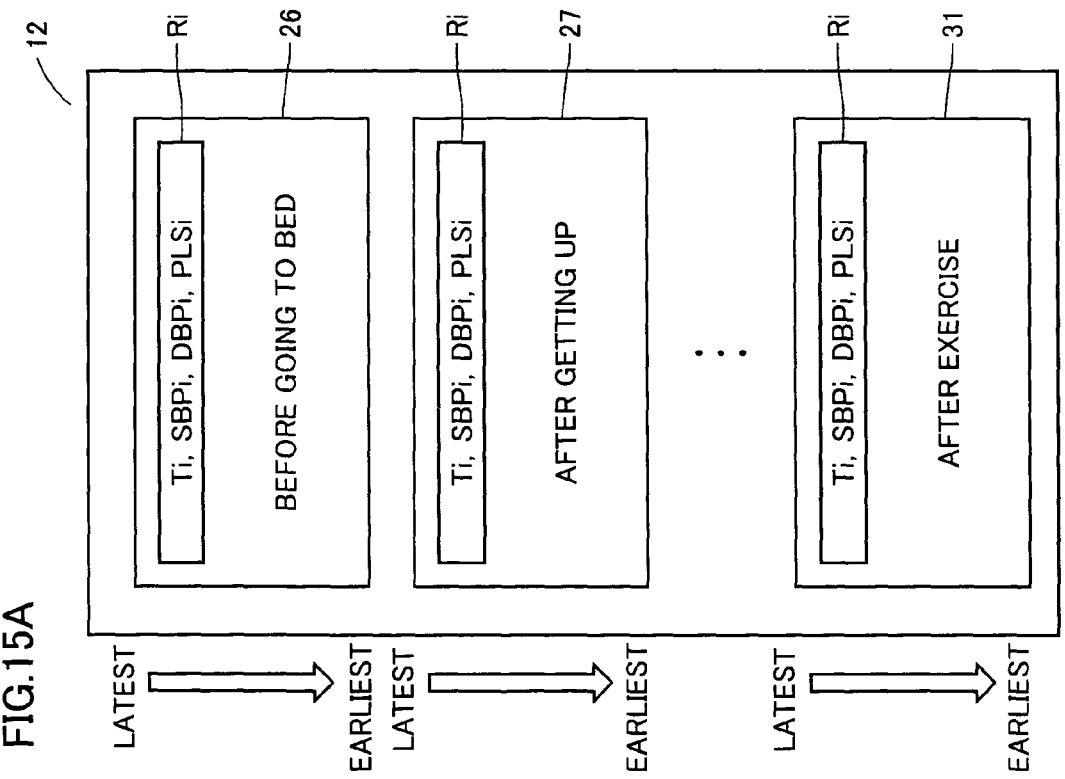

The content examples of memory 12 according to the present embodiment are shown in FIGS. 15A and 15B. As a specific example of storage in association with conditions, FIG. 15A shows a method of grouping records Ri of measurement result data based on the conditions designated at the time of blood pressure measurement, and storing them in areas 26, 27, ..., 31 provided in advance in memory 12 for the respective groups. The measurement results are stored in areas 26, 27, ..., 31 in units of records Ri. Record Ri includes measurement time data Ti, systolic blood pressure data SBPi indicating the systolic blood pressure, diastolic blood pressure data DBPi indicating the diastolic blood pressure, and pulse rate data PLSi indicating the pulse rate. The storage manner of the data is not restricted to the one using records Ri. All that is needed is that every time measurement is carried out, the data are stored in the respective areas in such a manner that the measurement values are associated with the relevant measurement.

In each area in FIG. 15A, records Ri are stored in a similar manner as in FIG. 6, in accordance with the order from the latest to the earliest.

It is assumed in the following explanation that measurement result data such as blood pressure values are grouped based on the measurement conditions and stored in respective memory areas, as shown in FIG. 15A. The method of associating the measurement result data with the conditions, however, is of course not limited to such a method. For example, it may be configured such that the measurement result data such as blood pressure values and the conditions are stored in pairs in memory 12, as shown in FIG. 15B. In FIG. 15B, a record RRi (i=1, 2, 3, ..., m) storing measurement result data such as a blood pressure value and information of a measurement condition as a pair, is stored in memory 12 every time blood pressure measurement is conducted. Record RRi stores measurement time data Ti, systolic blood pressure data SBPi, diastolic blood pressure data DBPi, pulse rate data PLSi, and one of condition data C1-C6. Condition data C1-C6 represent the measurement condition information indicated by corresponding switches 53-58 in condition switch group 50 manipulated at the time of blood pressure measurement, i.e., the measurement time zones of after getting up, before going to bed, before meal, after meal, before exercise, and after exercise, respectively. Letters indicating the corresponding conditions are printed on the surfaces of switches 53-58, so that the subject can easily associate the desired condition with the switch to be manipulated.

When the subject manipulates any of switches 53-58 corresponding to the respective conditions, i.e., after getting up, before going to bed, before meal, after meal, before exercise, and after exercise, so as to input the condition, a different manipulation signal for each switch manipulated is applied from manipulation portion 40 to CPU 20. It is assumed that data associating the manipulation signals with the areas (address spaces) are stored in a table (not shown) in data storing portion 30 or the like. Thus, data storing portion 30 can specify one of the plurality of areas 26, 27, ..., 31 in memory 12 by checking the table based on the applied manipulation signal.

Procedure of blood pressure measurement according to the present embodiment will now be described with reference to the flowchart in FIG. 13.

Firstly, the processing in steps ST1-ST8 are carried out in a similar manner as in FIG. 3. When confirming the blood pressure measurement result displayed in ST8, the subject manipulates a switch in condition switch group 50 corresponding to a desired condition (ST9a). Data storing portion 30 determines the designated condition based on the signal of the manipulated switch. Data storing portion 30 then generates a record Ri storing measurement result data and measurement time data, searches memory 12 based on the determined condition, and additionally stores the relevant record Ri in the area corresponding to the condition (ST9b). This enables association of record Ri of the measurement result data with the condition.

Although the switch manipulation for designating the condition is conducted at the end of the blood pressure measurement in FIG. 13, it may be conducted before the start of the blood pressure measurement, for example between the processing of ST1 and ST2.

Procedure of recalling the blood pressure measurement data in the designated area of memory 12 in order from the latest to the earliest is shown in FIG. 14. Firstly, the subject manipulates recall switch 44 (ST11). In response to application of a signal designating the manipulation, read and display portion 25 of CPU 20 is activated. Subsequently, the subject manipulates a switch in condition switch group 50 that corresponds to a condition of the measurement result data he/she wishes to recall (ST11a). Read and display portion 25 determines the designated condition based on a manipulation signal from the manipulated switch, searches memory 12 based on the determined condition, and selects (specifies) the area corresponding to the relevant condition (ST13a). It then retrieves and reads record Ri stored most recently (e.g., record Ri registered at the leading address of the area) from the selected area (ST13b), and displays the measurement result based on the content of the read record Ri on display portion 4, as shown in FIG. 16 (ST14).

In FIG. 16, for example, switch 54 indicating "before going to bed" in condition switch group 50 is manipulated, and thus, in a list 71 of names of conditions displayed on display portion 4, "before going to bed" alone is displayed in a different manner (in reversed mode or the like). This clearly shows that the measurement condition corresponding to the blood pressure measurement result data concurrently displayed on display portion 4 is "before going to bed". Display of list 71 of names of the measurement conditions may be replaced with LED or the like. In this case, for example, only the LED of the relevant measurement condition is turned on (while the other LED are off).

Thereafter, if a condition switch is not manipulated by the subject (NO in ST15a), the process is terminated. If manipulated (YES in ST15), read and display portion 25 determines whether the manipulated switch is the same as the one manipulated most recently (in ST13a), based on a result of comparison between the type of the switch indicated by the manipulation signal received in ST13a and the type of the switch indicated by the manipulation signal currently received (ST15b). It is noted that read and display portion 25 has a function to determine the type of the manipulated switch based on the manipulation signal applied, and also has a function to temporarily store the type of the switch thus determined.

As a result of comparison, if it determines that both manipulation signals designate the same switch type (YES in ST15b), it searches the currently selected area and reads the next latest measurement result data (ST17). For example, it reads the measurement result data stored in the next address in the selected area. Thereafter, the process proceeds to ST14, and the subsequent processing is carried out in a similar manner.

If it determines from the comparison result that the manipulation signals designate different switch types (NO in ST15b), it newly selects (specifies) an area in memory 12 based on the manipulation signal from the manipulated switch (ST13a). The subsequent processing is carried out in a similar manner for the measurement result data stored in the newly selected area.

In this manner, the loop processing of ST17, ST14, ST15a, ST15b is repeatedly carried out every time the same condition switch is manipulated. Records Ri are read from the selected area in memory 12 of FIG. 15A in order from the latest to the earliest, and their contents are displayed. Each switch in condition switch group 50 is used both for designating the condition at the time of blood pressure measurement and at the time of recalling the measurement result, and for instructing the recall itself of the measurement result data from memory 12.

In FIG. 14, read and display portion 25 is activated in response to manipulation of recall switch 44 (ST11). Alternatively, the manipulation of recall switch 44 may be omitted. More specifically, it may be configured such that, when the device is not in the blood pressure measurement mode with manipulation of start/stop switch 41 as shown in FIG. 13, read and display portion 25 is activated when any switch in condition switch group 50 is manipulated, and read and display portion 25 starts the processing shown in ST11a in FIG. 14.

It is noted that in the present embodiment, as in the case of the second embodiment, a reference value of blood pressure for each measurement condition may be set, and the reference value may be compared with a measured value to allow notification based on the comparison result.

Fourth Embodiment

Figure 17:
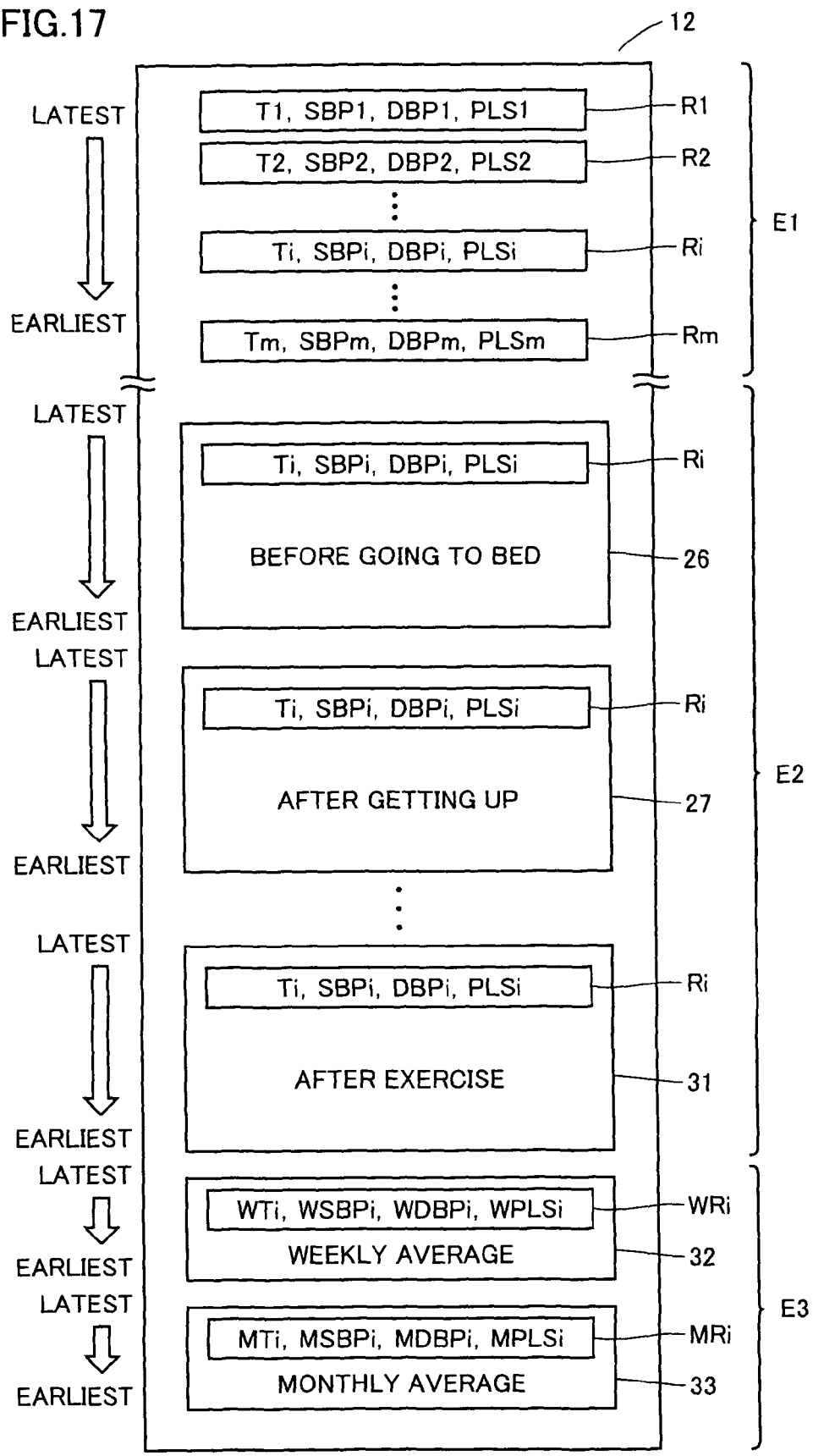
FIG. 17 shows a data storage example according to a fourth embodiment.

FIG. 17 shows a content example of memory 12 according to the present embodiment. Referring to FIG. 17, memory 12 includes areas E1, E2 and E3. In area E1, blood pressure measurement data (records Ri) are stored as in FIG. 6. In area E2, memory areas for the respective conditions are provided in advance as in FIG. 15A, and blood pressure measurement data (records Ri) are stored in the respective memory areas. Area E3 has a weekly average area 32 and a monthly average area 33.

When a weekly average switch 59 or a monthly average switch 60, as will be described later, is manipulated at a prescribed timing (for each blood pressure measurement, or for each prescribed period counted by timer 13), average calculation portion 281 of calculation portion 28, in receipt of a signal indicating the manipulation, reads systolic blood pressure data SBPi, diastolic blood pressure data DBPi and pulse rate data PLSi of records Ri stored in area E1 of memory 12, and calculates a weekly average for each read data, or a monthly average for each read data. It then generates a record WRi in which systolic blood pressure data WSBPi, diastolic blood pressure data WDBPi and pulse rate data WPLSi each indicating the thus calculated weekly average are associated with time data WTi. The generated record WRi is stored by data storing portion 30 in weekly average area 32 in memory 12. Similarly, it generates a record MRi in which systolic blood pressure data MSBPi, diastolic blood pressure data MDBPi and pulse rate data MPLSi are associated with time data MTi. The generated record MRi is stored by data storing portion 30 in monthly average area 33 in memory 12.

Records WRi and MRi indicating the average values are stored in weekly average area 32 and monthly average area 33, respectively, provided in advance in memory 12, in order from the latest data to the earliest data. Time data WTi indicates time that represents the week shown by data Ti of records Ri used for calculating the corresponding systolic blood pressure data WSBPi, diastolic blood pressure data WDBPi and pulse rate data WPLSi. For example, time data Ti indicating the first day from among data Ti of records Ri used for calculating the average may be designated therefor. Similarly, time data MTi may be set to be indicated by time data Ti indicating the first day from among data Ti of records Ri used for calculating the average. As such, the condition concerning the blood pressure data may be weekly average or monthly average.

Figure 18:
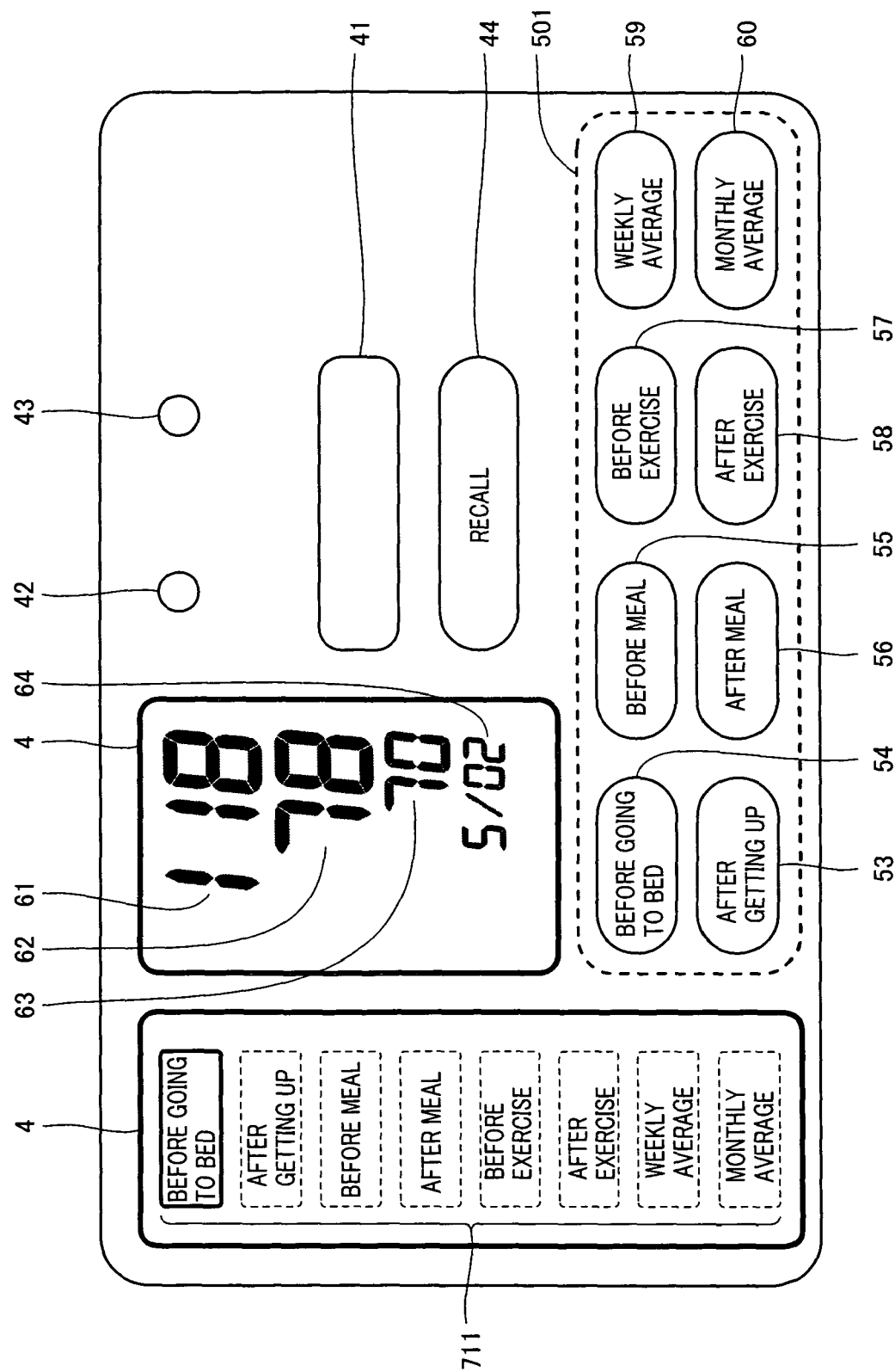
FIG. 18 shows a data display example and a condition switch group according to the fourth embodiment.

As shown in FIG. 18, manipulation portion 40 is provided with a condition switch group 501 in place of condition switch group 50. Condition switch group 501 includes, in addition to the switches included in condition switch group 50, a weekly average switch 59 and a monthly average switch 60. Further, display portion 4 displays a list 711 of names of conditions in place of list 71. List 711 of names of conditions displays the names of conditions corresponding to the respective switches in condition switch group 501.

In operation, every time weekly average switch 59 is manipulated, a signal indicating the manipulation of the switch is applied to CPU 20. In response to application of the manipulation signal, read and display portion 25 searches area 32 and recalls records WRi of the weekly average data in order by which they were measured and averaged (i.e., in order of storage). For example, it reads records WRi sequentially from the leading address of area 32. Thus, on the display, the weekly average data (average systolic blood pressure data, average diastolic blood pressure data, average pulse rate data) are displayed in chronological sequence from the latest data to the earliest data. Similarly, every time monthly average switch 60 is manipulated, read and display portion 25 searches area 33 and recalls records MRi of the monthly average data in order of measurement and calculation of the average (i.e., in order of storage). For example, it reads records MRi sequentially from the leading address of area 33. As such, on the display, the monthly average data (average systolic blood pressure data, average diastolic blood pressure data, average pulse rate data) are displayed in chronological sequence from the latest data to the earliest data. When recalling record WRi or MRi from weekly average area 32 or monthly average area 33, read and display portion 25 displays, together with the data of record WRi or MRi, the name of the corresponding condition in list 711 of names of conditions in a manner different from that of the other names. Accordingly, it is readily possible to confirm whether the blood pressure data being displayed is the weekly average or the monthly average.

According to each of the above embodiments, switches are provided corresponding to the respective measurement conditions for recalling memories, such as morning switch 51, evening switch 52 and other switches in condition switch group 50. Accordingly, it is possible to recall only the measurement result data satisfying a desired measurement condition, by simply manipulating the switch corresponding to the desired measurement condition, without the need of special manipulation for setting the measurement condition.

Further, the subject can intuitively understand the manipulation for recalling the measurement result data corresponding to the measurement condition desired to be recalled.

Furthermore, the measurement result data are recalled in accordance with the order of measurement (in order of storage). Thus, on the display, the blood pressure measurement result data are displayed in chronological sequence from the latest data to the earliest data. This allows the subject to confirm the trend of the measured blood pressure data on the display.

Fifth Embodiment

In the present embodiment, data of blood pressure measurement results stored in memory 12 of FIG. 1 in accordance with any of the above-described embodiments are transferred to another apparatus, and the recalling function according to any of the above embodiments is realized in the other apparatus. The other apparatus may be another electronic blood pressure monitor 1, or a data processing apparatus such as a computer.

The recalling function when the other apparatus is electronic blood pressure monitor 1 is as described in each of the above embodiments. Herein, explanation will be made assuming that the other apparatus is a data processing apparatus 130 that is a computer.

Figure 19:
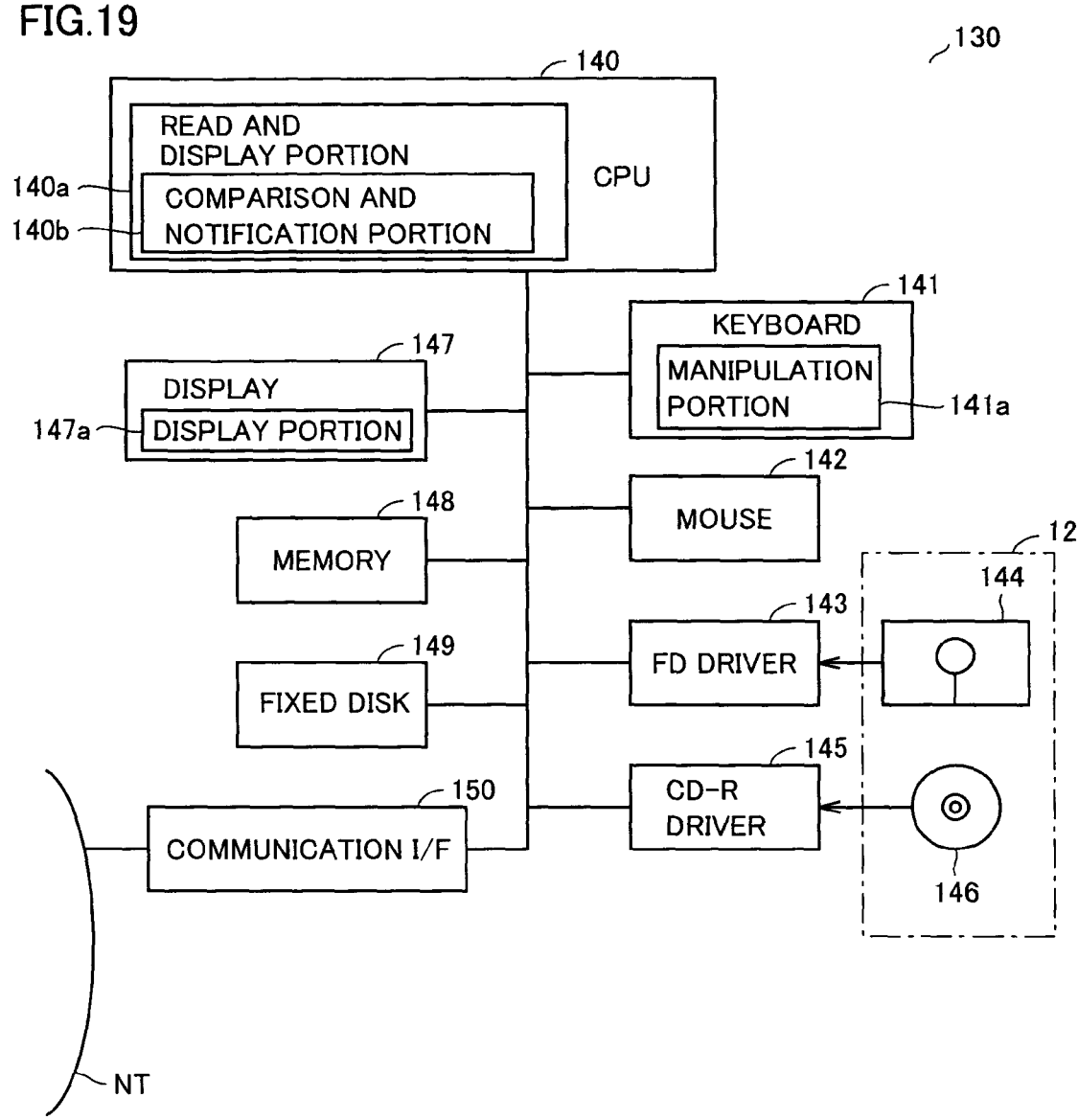
FIG. 19 is a configuration diagram of a computer according to a fifth embodiment.

Referring to FIG. 19, data processing apparatus 130 according to the present embodiment includes a display 147 formed of LCD (Liquid Crystal Display), CRT (Cathode Ray Tube) or the like, an input portion having a keyboard 141 and a mouse 142, a CPU 140 for centrally controlling data processing apparatus 130 itself, a memory 148 configured to include ROM (Read Only Memory) or RAM (Random Access Memory), a fixed disk 149, a FD (Flexible Disk) driver 143 mounted detachably with a FD 144 and accessing the mounted FD 144, a CD-R (Compact Disc Recordable) driver 145 mounted detachably with a CD-R 146 and accessing the mounted CD-R 146, and a communication I/F 150 for communicably connecting data processing apparatus 130 with a communication line NT. The respective portions are connected via a bus in a communicable manner. It is noted that the detachable recording medium is not limited to FD 144 or CD-R 146. It may be a card-type recording medium such as an IC (Integrated Circuit) card.

The recalling function of the blood pressure measurement data shown in FIGS. 4, 5, 11 and 14 above is realized by a program. In the present embodiment, the program is stored in a computer-readable recording medium in FIG. 19. The recording medium may be memory 148, or may be FD 144 or CD-R 146. In any case, the program recorded on the recording medium may be read and executed by CPU 140. Alternatively, it may be read and loaded to a prescribed program memory area (e.g., prescribed area in memory 148) in FIG. 19, and then read from the relevant area and executed by CPU 140. Further, the program may be downloaded from the outside via communication I/F 150 and communication line NT to memory 148 or the like.

CPU 140 includes a read and display portion 140a having a comparison and notification portion 140b. Read and display portion 140a and comparison and notification portion 140b have the functions equivalent to those of the above-described read and display portion 25 and comparison and notification portion 251, respectively. The functions of read and display portion 104a and comparison and notification portion 140b are realized as CPU 140 reads the program from the memory and executes the same.

Keyboard 141 has a manipulation portion 141a. Manipulation portion 141a includes condition switch group 50 or 501, and recall switch 44.

Display 147 includes a display portion 147a. Display portion 147a has the function equivalent to that of display portion 4 in each of the above embodiments.

It is assumed that memory 12 storing the measured blood pressure data in each of the above embodiments may be mounted to electronic blood pressure monitor 1 in a detachable manner. In such a case, memory 12 is mounted to data processing apparatus 130 in FIG. 19 as FD 144 or CD-R 146. As such, the blood pressure measurement data associated with conditions in the above embodiments are supplied to data processing apparatus 130.

Alternatively, data processing apparatus 130 may receive the blood pressure measurement data associated with conditions, which are read from memory 12 and transmitted by electronic blood pressure monitor 1, via communication line NT and communication I/F 150, and store the received data in FD 144 or CD-R 146. As such, the blood pressure measurement data associated with conditions in the above embodiments are supplied to data processing apparatus 130. Alternatively, in the case where the blood pressure data and the condition data are transmitted separately, the received blood pressure data may be stored in FD 144 or CD-R 146 in association with the received condition data.

When the blood pressure measurement data associated with conditions are supplied, the subject can manipulate recall switch 44 and condition switch group 50 or 501 in manipulation portion 141a in a similar manner as in the above embodiments, to display the blood pressure measurement data (including the average data) associated with a desired condition by display portion 147a of display 147.

As described above, the recalling function of the blood pressure measurement data explained in conjunction with electronic blood pressure monitor 1 is similarly applicable to data processing apparatus 130. Therefore, the subject can recall his/her blood pressure measurement data by manipulating data processing apparatus 130 even if he/she is away from home.

Although the present invention has been described and illustrated in detail, it is clearly understood that the same is by way of illustration and example only and is not to be taken by way of limitation, the spirit and scope of the present invention being limited only by the terms of the appended claims.

What is claimed is:
1. An electronic blood pressure monitor, comprising:
a blood pressure measurement unit having a cuff fitted to a blood pressure measurement site, a pressure increasing/decreasing unit adjusting a pressure applied to said cuff, a pressure detecting unit detecting a pressure within said cuff adjusted by said pressure increasing/decreasing unit, and a blood pressure calculation unit calculating a blood pressure based on the detected pressure by said pressure detecting unit;
a memory;
a display unit;
a time-counting unit counting time;
a storing unit storing data of the blood pressure calculated by said blood pressure calculation unit in said memory in association with measurement time information indi- cating time of blood pressure measurement by said blood pressure measurement unit counted by said time-counting unit;

a manipulation unit configured to be manipulated by a user to designate each of a plurality of conditions concerning said blood pressure data, wherein the plurality of conditions includes measurement time parameters; and a read and display unit, when reading of said blood pressure data from said memory is instructed by manipulation of said manipulation unit, selectively reading, from said memory, based at least in part on the user designated measurement time parameters, said blood pressure data associated with said measurement time information satisfying said condition designated by the manipulation unit, and displaying the read blood pressure data on said display unit.

2. The electronic blood pressure monitor according to claim 1, wherein said read and display unit reads said blood pressure data corresponding to said condition data indicating said designated condition from said memory in chronological sequence based on said measurement time information associated, and displays the read blood pressure data on said display unit in accordance with said chronological sequence.

3. The electronic blood pressure monitor according to claim 1, wherein said read and display unit has a comparison and notification unit comparing said blood pressure data read from said memory with reference blood pressure data and notifying of a comparison result.

4. The electronic blood pressure monitor according to claim 1, wherein said plurality of conditions include a condition indicating measurement in the morning and a condition indicating measurement in the evening.

5. The electronic blood pressure monitor according to claim 1, wherein said blood pressure calculation unit has an average calculation unit calculating weekly average data and/or monthly average data of said blood pressure data stored in said memory, and said plurality of conditions include a condition indicating measurement of said weekly average and/or a condition indicating measurement of said monthly average.

6. An electronic blood pressure monitor comprising:

a blood pressure measurement unit having a cuff fitted to a blood pressure measurement site, a pressure increasing/decreasing unit adjusting a pressure applied to said cuff, a pressure detecting unit detecting a pressure within said cuff adjusted by said pressure increasing/decreasing unit, and a blood pressure calculation unit calculating a blood pressure based on the detected pressure by said pressure detecting unit;

a memory;

a display unit;

a plurality of manipulation units each corresponding to each of a plurality of conditions concerning blood pressure data and manipulated for designating the corresponding condition, wherein at least one of the manipulation units is configured to allow a user to input measurement time parameters;

a storing unit storing, in said memory, data of the blood pressure calculated by said blood pressure calculation unit at the time of blood pressure measurement by said blood pressure measurement unit, in association with condition data indicating said condition corresponding to said manipulation unit manipulated at the time of the blood pressure measurement; and a read and display unit, in response to manipulation of said manipulation unit and said input measurement time parameters, selectively reading, from said memory, said blood pressure data associated with said condition data indicating said condition designated by the manipulation unit, and displaying the read blood pressure data on said display unit.

7. The electronic blood pressure monitor according to claim 6, wherein said plurality of conditions include a condition indicating measurement after getting up and a condition indicating measurement before going to bed.

8. The electronic blood pressure monitor according to claim 6, wherein said plurality of conditions include a condition indicating measurement before meal and a condition indicating measurement after meal.

9. The electronic blood pressure monitor according to claim 6, wherein said plurality of conditions include a condition indicating measurement before exercise and a condition indicating measurement after exercise.

10. The electronic blood pressure monitor according to claim 6, wherein said plurality of conditions include a condition indicating measurement before medication and a condition indicating measurement after medication.

11. The electronic blood pressure monitor according to claim 6, wherein said read and display unit has a comparison and notification unit comparing said blood pressure data read from said memory with reference blood pressure data and notifying of a comparison result.

12. The electronic blood pressure monitor according to claim 6, wherein said blood pressure calculation unit has an average calculation unit calculating weekly average data and/or monthly average data of said blood pressure data stored in said memory, and said plurality of conditions include a condition indicating measurement of said weekly average and/or a condition indicating measurement of said monthly average.

13. A data processing apparatus, comprising:

a storing unit storing data of a blood pressure calculated with blood pressure measurement in a prepared memory in association with measurement time information indicating time of the blood pressure measurement;

a manipulation unit configured to be manipulated by a user to designate each of a plurality of conditions concerning said blood pressure data, wherein the plurality of conditions includes measurement time parameters; and a read and display unit, when reading of said blood pressure data from said memory is instructed by manipulation of said manipulation unit, selectively reading, from said memory, based at least in part on the user designated measurement time parameters, said blood pressure data associated with said measurement time information satisfying said condition designated by the manipulation unit, and displaying the read blood pressure data on a prepared display unit.

14. A data processing apparatus, comprising:

a memory having data of a blood pressure calculated with blood pressure measurement stored in association with condition data indicating a condition concerning the blood pressure data;

a manipulation unit corresponding to each of a plurality of conditions concerning said blood pressure data and configured to be manipulated by a user to designate the corresponding condition, wherein the plurality of conditions includes measurement time parameters; and a read and display unit, in response to manipulation of said manipulation unit, selectively reading, from said memory, based at least in part on the user designated measurement time parameters, said blood pressure data associated with said condition data indicating said condition designated by the manipulation unit, and displaying the read data on a prepared display unit.

15. A data processing method of an electronic blood pressure monitor including a blood pressure measurement unit having a cuff fitted to a blood pressure measurement site, a pressure increasing/decreasing unit adjusting a pressure applied to said cuff, a pressure detecting unit detecting a pressure within said cuff adjusted by said pressure increasing/decreasing unit, and a blood pressure calculation unit calculating a blood pressure based on the detected pressure by said pressure detecting unit, a memory, a display unit, a time-counting unit counting time, and a manipulation unit configured to be manipulated by a user to designate each of a plurality of conditions concerning said blood pressure data, wherein the plurality of conditions includes measurement time parameters, said data processing method comprising the steps of:

storing said blood pressure data calculated by said blood pressure calculation unit in said memory in association with measurement time information indicating time of blood pressure measurement by said blood pressure measurement unit counted by said time-counting unit; and when reading of said blood pressure data from said memory is instructed by manipulation of said manipulation unit, selectively reading, from said memory, based at least in part on the user designated measurement time parameters, said blood pressure data associated with said measurement time information satisfying the condition concerning said blood pressure data designated by the manipulation unit, and displaying the read blood pressure data on said display unit.

* * * * *